(12) United States Patent
Nishichi et al.

(10) Patent No.: US 7,589,228 B2
(45) Date of Patent: *Sep. 15, 2009

(54) FLUORINE-CONTAINING COMPOUND

(75) Inventors: Ai Nishichi, Osaka (JP); Yoshinobu Asako, Hyogo (JP); Kazushi Omote, Nara (JP); Shimpei Sato, Osaka (JP); Toshiya Iida, Osaka (JP); Satoshi Ishida, Kyoto (JP)

(73) Assignee: Nippon Shokubai Co., Ltd., Osaka-Shi (JP)

( * ) Notice: Subject to any disclaimer, the term of this patent is extended or adjusted under 35 U.S.C. 154(b) by 602 days.

This patent is subject to a terminal disclaimer.

(21) Appl. No.: 10/908,849

(22) Filed: May 27, 2005

(65) Prior Publication Data

US 2005/0265686 A1  Dec. 1, 2005

(30) Foreign Application Priority Data

| May 28, 2004 | (JP) | ............................... 2004-160154 |
| Aug. 3, 2004 | (JP) | ............................... 2004-226815 |
| Nov. 29, 2004 | (JP) | ............................... 2004-344273 |
| Dec. 1, 2004 | (JP) | ............................... 2004-349160 |

(51) Int. Cl.
   *C07C 69/76* (2006.01)
(52) U.S. Cl. ........................................ 560/53
(58) Field of Classification Search ............ 560/53
   See application file for complete search history.

(56) References Cited

U.S. PATENT DOCUMENTS

| 4,958,043 A | 9/1990 | Weaver et al. |
| 6,172,181 B1 | 1/2001 | Kimura et al. |

FOREIGN PATENT DOCUMENTS

| EP | 1 420 473 A1 | 5/2004 |
| JP | 05-032731 A | 2/1993 |
| JP | 2000-089049 A | 3/2000 |
| JP | 2000-239325 A | 9/2000 |
| JP | 2001-064226 A | 3/2001 |
| JP | 2003-082091 A | 3/2003 |
| WO | WO-03/037321 | 5/2003 |
| WO | WO-2004/100282 | 11/2004 |

OTHER PUBLICATIONS

Spratt et al., "*p*-Fluorobenzoyl Chloride for Characterization of Active Hydrogen Functional Groups by Fluorine-19 Nuclear Magnetic Resonance Spectrometry", *Analytical Chemistry*, 56(12), 2038-43 (1984).

Holger M. Kuch et al.; "Determination of Endocrine-Disrupting Phenolic Compounds and Estrogens in Surface and Drinking Water by HRGC—(NCI)—MS in the Picogram per Liter Range"; Environ. Sci. Technol. 2001, 35, pp. 3201-3206.

*Primary Examiner*—James O Wilson
*Assistant Examiner*—Ebenezer Sackey
(74) *Attorney, Agent, or Firm*—Connolly Bove Lodge & Hutz LLP

(57) ABSTRACT

The present invention has an object to provide a fluorine-containing compound which can be used for applications such as additives making a transparent resin material low in a water absorbing ratio and high in water repellency without deteriorating of various properties such as transparency which the transparent resin material has, a fluorine-containing ester compound which is superior in properties such as heat resistance and low moisture(water) absorption property and can be suitably used in various fields such as a material for electronic information, a material for precision instruments and an optical material, a fluorine-containing aryl ester polymer, methods of producing the same. The present invention provides a fluorine-containing compound represented by the following formula (1):

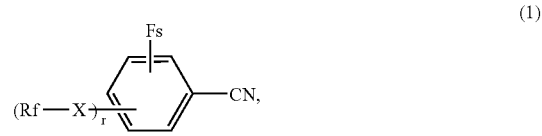

in the formula, X represents an oxygen atom or a sulfur atom; Rf represents a fluorine-containing alkyl group having 4 or more carbon atoms; r represents the number of Rf—X— groups bonded to an aromatic ring and is an integer of 1 or more; s represents the number of fluorine atoms bonded to an aromatic ring and is an integer of 1 or more; and r+s is an integer of 2 to 5.

6 Claims, 16 Drawing Sheets

FLUORINE-CONTAINING COMPOUND

BACKGROUND OF THE INVENTION

The present invention relates to a fluorine-containing compound. More particularly, the present invention relates to a fluorine-containing compound which can be used as additive for transparent resin material to be used for a variety of applications such as optical communication, optical waveguide, optical recording and a liquid crystal display, and relates to a formed body comprising the fluorine-containing compound to be used for a variety of applications such as optical communication, optical waveguide, optical recording, and liquid crystal display, and relates to material for optical and electronic part.

Fluorine-containing compound is useful compound which can exert excellent properties such as water repellency by virtue of a fluorine atom and employed as raw materials of various industrial products. And, as a technical field of fluorine chemicals, there is given the application to a transparent resin material used for optical communication, an optical waveguide, optical recording, a liquid crystal display and the like. Many of transparent resins which have been conventionally used in these applications exhibit a water absorbing property. And since the absorption of water into the transparent resin results in various adverse effects such as occurrence of warping and strains of molded(formed) body and increase of transmission loss, a variety of studies have been conducted on reduction in a water absorbing property of a transparent resin. With respect to the fluorine-containing compound capable of exerting properties resulting from a fluorine atom, there is noted its application to the transparent resin material to be used for the information technology (IT) field as the recent development of IT fields.

With respect to a material containing conventional transparent resin, for example, Japanese Kokai Publication 2000-239325 discloses resin compositions containing a polymer (A) containing a repeating unit of 6-membered ring structure having ether bond and a (meth)acrylic polymer (B), and Japanese Kokai Publication Hei-05-32731 discloses a low water-absorption transparent resin produced by injection polymerization of compositions containing phenyl methacrylate, dicyclopentenyl acrylate, and alkyl acrylate having alkyl group of 1 to 5 carbon atoms and crosslinking agent in the presence of a radical polymerization initiator. With respect to these resin compositions, there are descriptions that they are usable for optical parts such as lens, optical information recording media such as optical disk, and materials for optical transmission. Furthermore, for example, Japanese Kokai Publication 2000-89049 discloses polymer materials for optical communication which comprises a repeating unit consisted of ester-bonded compounds containing nitrogen atom in main chains.

However, there is a room for contrivance for providing the material containing these transparent resin with improved low water-absorption property and preferably usable for various applications such as optical communication, optical waveguide, optical recording, and liquid crystal display fields.

As conventional fluorine-containing polymers, fluorine-containing aryl ether ketone polymers are disclosed in Japanese Kokai Publication 2001-64226 and 2003-82091. These polymers comprise monomer units having a fluorine-substituted benzene ring and phenyl ether structure and exhibits basic properties such as solubility in solvent and heat resistance. However, there is a room for contrivance to provide fluorine-containing polymers with further improved properties so as to be suitably used for optical and electronic parts and additives for resin.

SUMMARY OF THE INVENTION

The present invention has been made in view of the above-mentioned state of the art and it is an object of the present invention to provide a fluorine-containing compound which can be used for applications such as additives making a transparent resin material low in a water absorbing ratio and high in water repellency without deteriorating of various properties such as transparency which the transparent resin material has, a fluorine-containing ester compound and a fluorine-containing aryl ester polymer which are superior in properties such as heat resistance and low moisture(water) absorption property and can be suitably used in various fields such as a material for electronic information, a material for precision instruments and an optical material, methods of producing the same, a formed body which comprises the same and a material for optical and electronic part using a fluorine-containing oxadiazole compound.

The present inventors have made various investigations of fluorine-containing compound and have found a novel fluorine-containing compound having a structure in which hydrogen atom of a benzene ring having cyano group as a substituent group is replaced with fluorine atom and one or more fluoroalkyl groups are bonded to the benzene ring through oxygen atom (O) or sulfur atom (S). And for example, when the compound is added to transparent resin such as acrylic resin, fluorine excellent in water repellency provides the transparent resin with lowered water absorption property and excellent water repellency and at the same time the refractive index of the transparent resin may be controlled without deteriorating various properties such as thermal properties which the transparent resin originally have and in addition, the present inventors have also found a producing method which can produce the fluorine-containing compound with a specified structure efficiently.

The present inventors further investigated fluorine-containing compounds preferably usable in various fields of electronic information material and optical material, and the present inventors also have found that when the fluorine-containing compound has a structure in which fluorine-substituted two benzene rings and divalent organic groups with a specified structure is bonded by ester bond, the compound is provided with excellent lower water absorption property and weathering resistance and also excellent in solubility in various solvents and high reactivity and therefore, polymer may be produced at a lower temperature than that required for polymerization reaction of conventional fluorine-containing compounds.

And the present inventors have found that polymer excellent in heat resistance, electric properties and other characteristics such as transparency, weathering resistance and water repellency as well as low water absorption property may be produced by reaction of such a fluorine-containing compound and a compound having two hydroxyl groups in one molecule, and that the polymers may be formed in various forms such as films, fibers, pellets, and sheets depending on the necessity in various fields of electronic information materials, precision machine materials, optical materials and preferably used, since the polymer are excellent in solubility in solvent. The inventors have also found that when the fluorine-containing compound and/or the fluorine-containing polymer are added as additives to resin, the addition can lower the water absorption property of the resin. Particularly, the inventors have found that, since the fluorine-containing compound and the fluorine-containing polymer have ester structure, they are excellent in compatibility with ester resin having ester bond in the structure, and when these compound and/or polymer are added to resin as additives, the addition more effectively lower the water absorption property of the resin. And the inventors have also found that the fluorine-containing compound and the fluorine-containing polymer may be used for a resin composition preferably usable in fields of optical communication, optical waveguide, optical recording, liquid crystal display and the like in which low water absorption resin are required for preventing various adverse effects caused by the water absorption of resin and also preferably usable for electronic information materials and precision machine materials. And the present inventors have found that the fluorine-containing compound, the fluorine-containing polymer, and the transparent resin materials of the present invention are excellent in refractive index and also use of these formed bodies makes precise control of the refractive index possible.

The present inventors have made more investigations of material to be preferably usable in the optical and electronic part fields and consequently have found that fluorine-containing polymer having the structural unit comprising a structure in which an oxadiazole ring is contained between fluorine-substituted two benzene rings and a structure derived from a diol compound are excellent in optical and electric properties such as transparency and dielectric constant as well as excellent in solubility in solvents, heat resistance, water repellency, and in addition, excellent in adhesive property and sticking property and that the material using the fluorine-containing oxadiazole polymer is preferably usable in the optical and electronic part fields, and accordingly, the inventors have reached the solution of the above-mentioned problems and have completed the present invention.

That is, the present invention provides a fluorine-containing compound represented by the following formula (1):

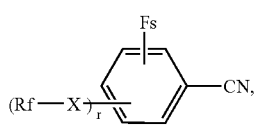
(1)

in the formula, X represents an oxygen atom or a sulfur atom; Rf represents a fluorine-containing alkyl group having 4 or more carbon atoms; r represents the number of Rf—X— groups bonded to an aromatic ring and is an integer of 1 or more; s represents the number of fluorine atoms bonded to an aromatic ring and is an integer of 1 or more; and r+s is an integer of 2 to 5.

The present invention also provides a method of producing a fluorine-containing compound represented by the following formula (1):

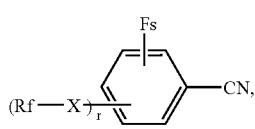
(1)

in the formula, X represents an oxygen atom or a sulfur atom; Rf represents a fluorine-containing alkyl group having 4 or more carbon atoms; r represents the number of Rf—X— groups bonded to an aromatic ring and is an integer of 1 or more; s represents the number of fluorine atoms bonded to an aromatic ring and is an integer of 1 or more; and r+s is an integer of 2 to 5, wherein the fluorine-containing compound is produced by reacting fluorine-containing alkyl alcohol having 4 or more carbon atoms or fluorine-containing alkyl thiol having 4 or more carbon atoms with fluorine-containing benzonitrile.

The present invention also provides a fluorine-containing ester compound represented by the following formula (3):

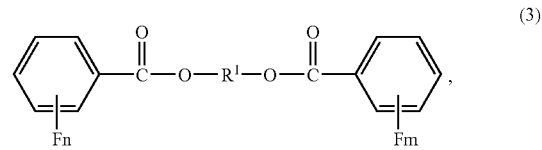
(3)

in the formula, m and n are same or different and each represents the number of fluorine atoms bonded to a benzene ring and is an integer of 0 to 5 and m+n is an integer of 1 or more; and $R^1$ represents a divalent organic group having 1 to 150 carbon atoms.

The present invention also provides a fluorine-containing aryl ester polymer which comprises a repeating unit represented by the following formula (6):

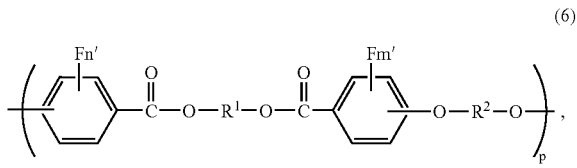
(6)

in the formula, m' and n' are same or different and each represents the number of fluorine atoms bonded to a benzene ring and is an integer of 0 to 4 and m'+n' is an integer of 1 or more; $R^1$ and $R^2$ are same or different and each represents a divalent organic group having 1 to 150 carbon atoms; and p represents a polymerization degree.

The present invention also provides a method of producing a fluorine-containing aryl ester polymer, wherein said method comprises the step of polymerizing the fluorine-containing ester compound represented by the following formula (3):

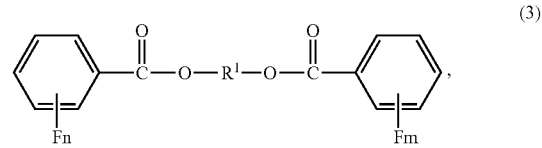
(3)

in the formula, m and n are same or different and each represents the number of fluorine atoms bonded to a benzene ring and is an integer of 0 to 5 and m+n is an integer of 1 or more; and $R^1$ represents a divalent organic group having 1 to 150 carbon atoms, with a dihydroxy compound represented by the following formula (9):

HO—$R^2$—OH (9)

in the formula, $R^2$ represents a divalent organic group having 1 to 150 carbon atoms, in the presence of a basic catalyst.

The present invention also provides a material for optical and electronic part which is formed by using a polymer having a fluorine-containing oxadiazole structural unit represented by the following formula (10):

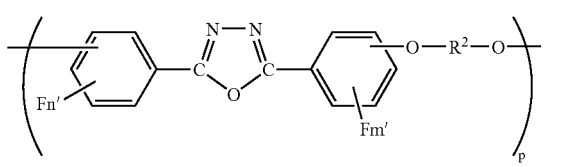

(10)

in the formula, m' and n' are same or different and each represents the number of fluorine atoms bonded to a benzene ring and is an integer of 0 to 4 and m'+n' is an integer of 1 or more; $R^2$ represents a divalent organic group having 1 to 150 carbon atoms; and p represents a polymerization degree.

DETAILED DESCRIPTION OF THE INVENTION

Figure 1:
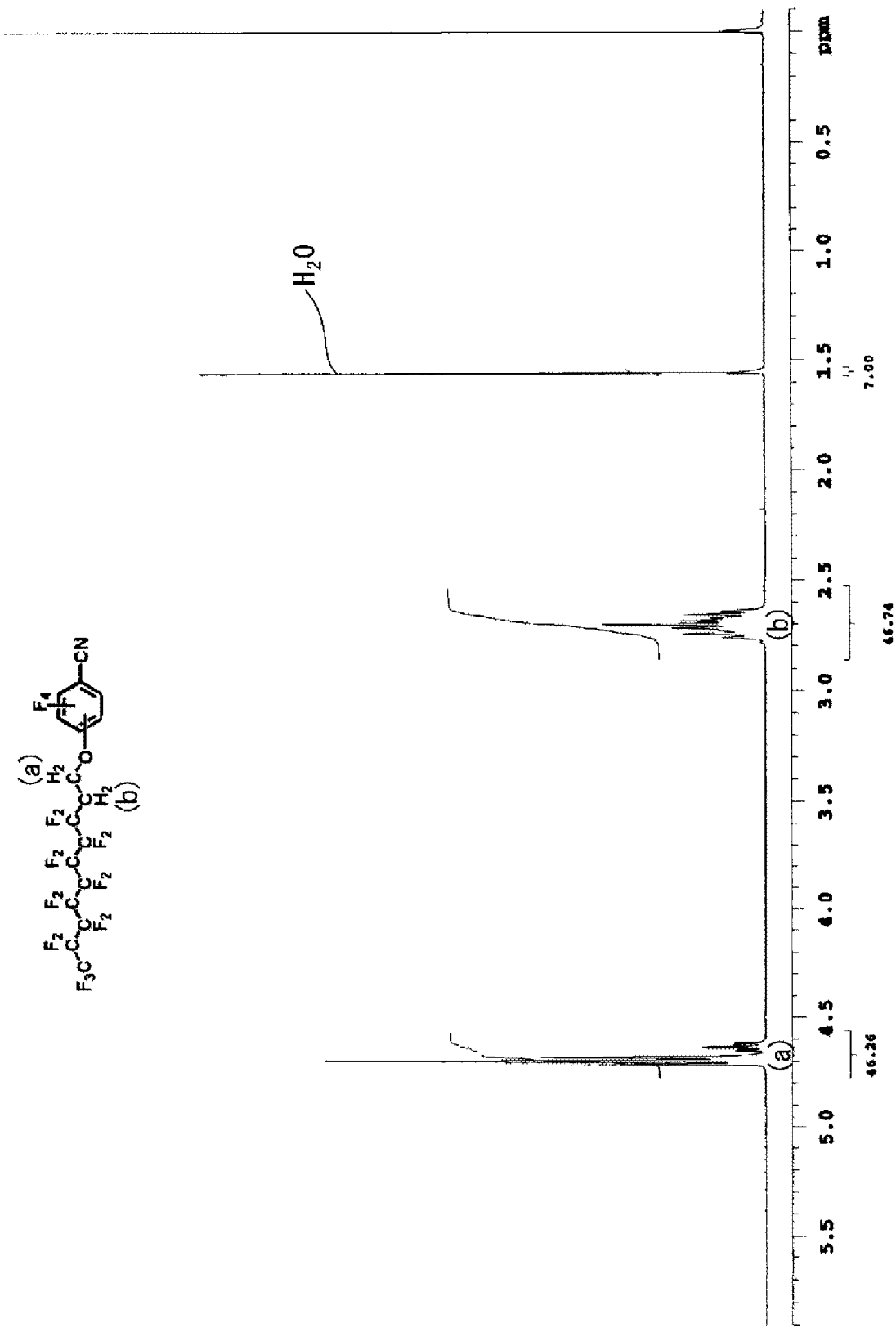
FIG. 1 shows a chart of $^1$H-NMR measurement of a mixture of heptadecafluorodecanoxy-2,3,5,6-tetrafluorobenzonitrile (p-isomer) and heptadecafluorodecanoxy-3,4,5,6-tetrafluorobenzonitrile (o-isomer), obtained in Synthetic Example 1 of the present invention.

Hereafter, the present invention will be described in detail.

in the fluorine-containing compound represented by the above-mentioned formula (1), the fluorine-containing alkyl group means those in which hydrogen atoms bonded to carbon atoms constituting an alkyl group are partially or entirely replaced with fluorine atoms, and the structure is not particularly limited and may be straight, branched, or cyclic alkyl and the number of fluorine atoms bonded to carbon atoms is preferably larger than that of hydrogen atoms bonded to carbon atoms. When the number of fluorine atoms is larger than that of hydrogen atoms, for example, in the case where the above-mentioned fluorine-containing compound is used as an additive for the transparent resin material, the transparent resin material may sufficiently exhibit water repellency. The fluorine-containing compound represented by the formula (1) in which r+s is 5, that is, fluorine atoms or Rf—X— is bonded to all carbon atoms of the aromatic ring is preferable. The case of r=1 and s=4 is more preferable.

One or two or more kinds of the fluorine-containing compound of the present invention may be added in the case where the compound is added to the transparent resin material.

Examples of the compound where r=1 and s=4 in the formula (1) may include compounds represented by the following formulae (1-1) to (1-6).

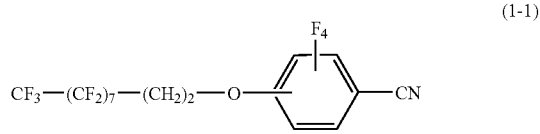

(1-1)

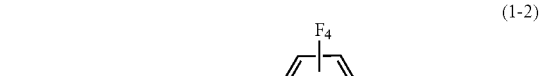

(1-2)

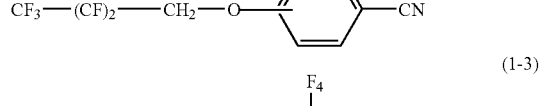

(1-3)

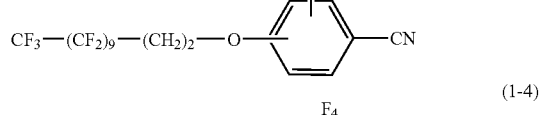

(1-4)

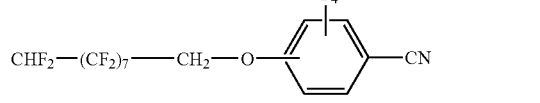

(1-5)

-continued

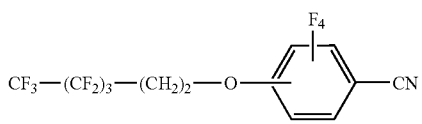
(1-6)

As the fluorine-containing compound represented by the above formula (1), among the fluorine-containing compounds represented by the above formula (1) in which r+s is 5, compound represented by the formula (2) are more preferable.

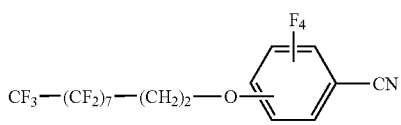
(2)

In the case where the fluorine-containing compound has such a structure, addition of the compound to the transparent resin material may provide the transparent resin material with further lowered water absorption property and more improved water repellency.

On of the present invention is a method of producing a fluorine-containing compound represented by the following formula (1):

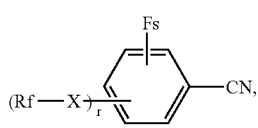
(1)

in the formula, X represents an oxygen atom or a sulfur atom; Rf represents a fluorine-containing alkyl group having 4 or more carbon atoms; r represents the number of Rf—X— groups bonded to an aromatic ring and is an integer of 1 or more; s represents the number of fluorine atoms bonded to an aromatic ring and is an integer of 1 or more; and r+s is an integer of 2 to 5, wherein the fluorine-containing compound is produced by reacting fluorine-containing alkyl alcohol having 4 or more carbon atoms or fluorine-containing alkyl thiol having 4 or more carbon atoms with fluorine-containing benzonitrile. By this producing method, it is possible to produce efficiently a compound in which hydrogen atom of an aromatic ring of the fluorine-containing benzonitrile is substituted with one or two or more fluorine-containing alkoxyl groups. In this reaction, each of the fluorine-containing alkyl alcohol having 4 or more carbon atoms and the fluorine-containing benzonitrile may be used alone or in combination of two or more species.

in the above reaction, a ratio of the usage of the fluorine-containing alkyl alcohol or the fluorine-containing alkyl thiol to the fluorine-containing benzonitrile may be appropriately determined depending on number of fluorine-containing alkoxyl groups or fluorine-containing alkylthio groups which add to the fluorine-containing compound produced by a reaction as a substituent groups. For example, when a mono-substituted product, produced by replacing a fluorine atom of an benzene ring of pentafluorobenzonitrile with one fluorine-containing alkyl group, is produced by reacting the fluorine-containing alkyl alcohol with the pentafluorobenzonitrile (PFBN), it is preferred to add the pentafluorobenzonitrile in the proportions of 1 to 5 mol relative to 1 mol of the fluorine-containing alkyl alcohol to react. It is more preferred to add the pentafluorobenzonitrile in the proportions of 1 to 2 mol relative to 1 mol of the fluorine-containing alkyl alcohol to react.

And, the above reaction is preferably performed in the presence of a basic catalyst. The basic catalyst is not particularly limited as long as it is a basic material capable of catching hydrogen fluoride (HF) in a reaction system, and potassium carbonate, calcium carbonate, lithium carbonate, potassium hydroxide, calcium hydroxide, potassium fluoride, triethylamine, tributylamine, pyridine and the like can be used. Amounts of the basic material to be used may also be appropriately determined depending on number of fluorine-containing alkoxyl groups or fluorine-containing alkylthio groups which add to the fluorine-containing compound produced by a reaction as a substituent groups. For example, when a mono-substituted product, produced by replacing a fluorine atom of an benzene ring of pentafluorobenzonitrile with one fluorine-containing alkyl group, is produced as a product, the amount of the basic material to be used is preferably 0.5 to 5 mol relative to 1 mol of the pentafluorobenzonitrile. It is more preferably 0.5 to 1 mol. These basic material may be used alone or in combination of two or more species.

As a solvent which can be used in the above reaction, there are given nitriles such as acetonitrile, benzonitrile, etc.; ketones such as acetone, methyl isobutyl ketone (MIBK), methyl ethyl ketone (MEK), cyclohexanone, etc.; halogenated hydrocarbons such as chloroform, methylene chloride, carbon tetrachloride, chloroethane, dichloroethane, trichloroethane, tetrachloroethane, etc.; aromatic hydrocarbons such as benzene, toluene, xylene, etc.; hydrocarbons such as pentane, hexane, cyclohexane, heptane, etc.; ethers such as diethyl ether, isopropyl ether, tetrahydrofuran (THF), dioxane, diphenyl ether, benzyl ether, tert-butyl ether, etc.; esters such as methyl formate, ethyl formate, methyl acetate, ethyl acetate, propyl acetate, isopropyl acetate, etc.; nitros such as nitrobenzene, nitromethane, etc.; N-methyl-2-pyrrolidone (NMP), dimethylformamide (DMF), dimethyl sulfoxide (DMSO), dimethylacetamide (DMAc) and the like. These solvents may be used alone or in combination of two or more species.

The concentration of the fluorine-containing benzonitrile in these solvents is preferably 1 to 40% by mass (% by weight). When the concentration of the fluorine-containing benzonitrile in the solvent is out of this range, efficiency of a reaction will decrease. This content is more preferably 5 to 30% by mass.

Reaction conditions of the above reaction is not particularly limited, but as a reaction temperature, a temperature of 0 to 150° C. is preferred and as a reaction time, one or more hours is preferred. By carried out the reaction under these conditions, the fluorine-containing compound described above can be obtained at a high yield. And the reaction may be done under normal pressure or under reduced pressure.

A product produced by the above reaction can be obtained by being separated from another components by a method, for example, in which after removing precipitated salt, a solvent is distilled off and then the remaining solution is distilled, or a solvent is distilled off and then the product is extracted from the remaining solution with an organic solvent and separated with a column chromatography.

The fluorine-containing compound of the present invention represented by the above formula (1) may be used preferably as an additive for transparent resin material.

When the fluorine-containing compound of the present invention represented by the above formula (1) is used as an additive for the transparent resin material, not only the transparent resin is provided with further lowered water absorption property and improved water repellency attributed to the excellent water repellency of fluorine atom but also the refractive index of the transparent resin material may be changed depending on the content of the additive without deteriorating the various properties such as thermal properties by properly setting the content of the fluorine-containing compound.

The above-mentioned transparent resin material comprises a polymer to form a formed body having transparency. As the transparent resin material, any material which can form a formed body having transparency can be used. And examples of the material are acrylic resin, polycarbonate resin, fluoro resin, epoxy resin, polyether resin, polyester resin, polyallylate resin, cycloolefin resin, norbornene resin, polyimide resin, silicon resin, polysulfone resin, and polyketone resin.

The above-mentioned transparency refers to having high light transmittance. The transparent resin material referred to herein means a substance having a total luminous transmittance of 70% or higher. As for a method of measuring the light transmittance, there can be given a method of using a colorimeter NDH-1001 DP type (manufactured by Nippon Denshoku Industries Co., Ltd.) as a measuring apparatus.

A fluorine-containing ester compound of the present invention is a compound having a structure represented by the following formula (3):

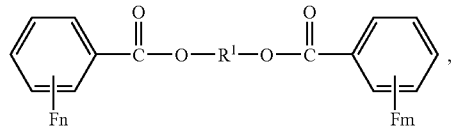
(3)

in the formula, m and n are same or different and each represents the number of fluorine atoms bonded to a benzene ring and is an integer of 0 to 5 and m+n is 1 or more; and $R^1$ represents a divalent organic group having 1 to 150 carbon atoms. The number of fluorine atoms bonded to a benzene ring may be any of 1 to 5, but it is preferably 3 to 5. It is more preferred that it is 5, that is, that fluorine atoms bond to all carbon atoms other than a carbon atom in the form of an ester bond among six carbon atoms of a benzene ring. In addition, another substituent group such as a halogen atom other than a fluorine atom, a substituent group having an alkyl chain and the like may bond to the benzene ring.

In the above formula (3), $R^1$ represents a divalent organic group having 1 to 150 carbon atoms, but the divalent organic group is preferably an organic group having 1 to 50 carbon atoms. It is more preferably any of the groups represented by the following formulae (11-1) to (11-18).

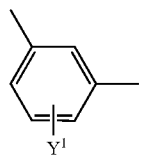
(11-1)

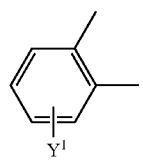
(11-2)

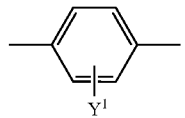
(11-3)

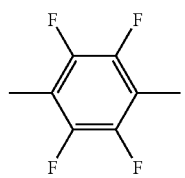
(11-4)

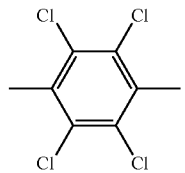
(11-5)

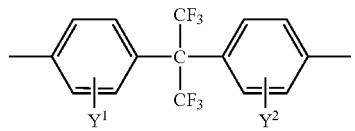
(11-6)

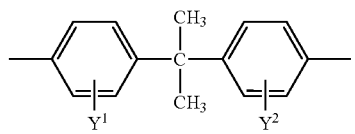
(11-7)

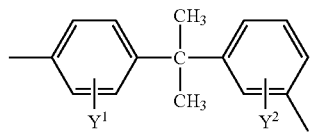
(11-8)

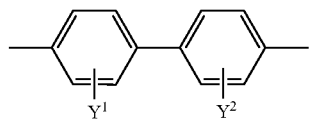
(11-9)

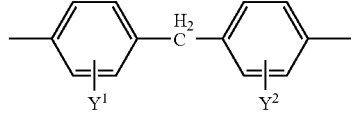
(11-10)

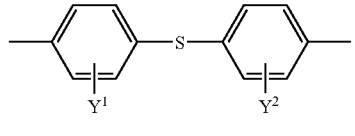
(11-11)

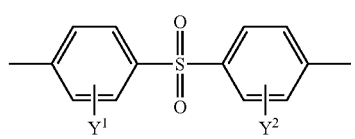
(11-12)

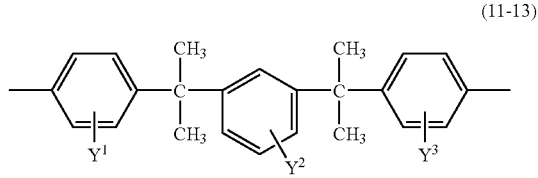
(11-13)

-continued (11-14)
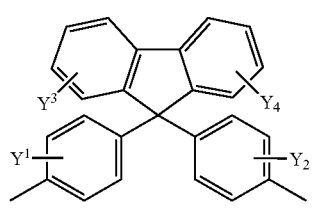

(11-15)
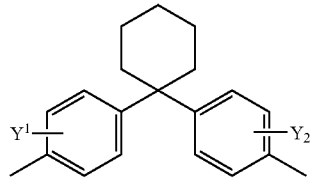

(11-16)
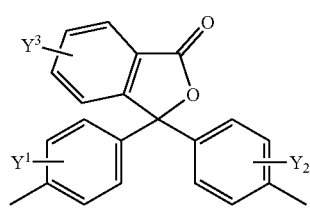

(11-17)
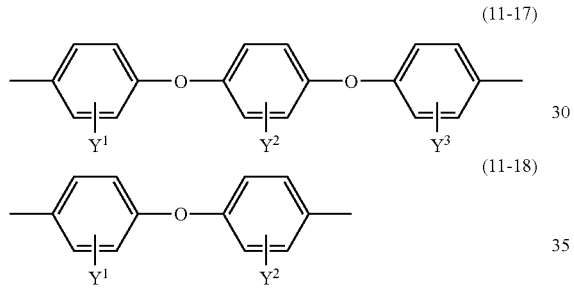

(11-18)
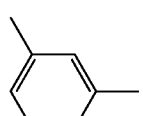

In the above formulas (11-1) to (11-18), $Y^1$, $Y^2$, $Y^3$ and $Y^4$ are same or different and each represents substituent group, and a benzene ring has one to four of $Y^1$, $Y^2$, $Y^3$ and $Y^4$ as a substituent group. As the substituent group represented by $Y^1$, $Y^2$, $Y^3$ and $Y^4$, for example, an alkyl group, an alkoxy group, an alkylamino group, an alkylthio group, an aryl group, an aryloxy group, an arylamino group, an arylthio group, which each may contain a substituent group, and a halogen atom, etc. are suitable. An alkyl group, an alkoxy group, which has 1 to 30 carbon atoms and each may contain a substituent group, and a halogen atom are preferred.

In the fluorine-containing ester compound of the present invention, the groups represented by the above formulae (11-1) to (11-18) are preferably groups represented by the following formulae (12-1) to (12-19).

(12-1)
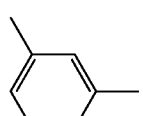

(12-2)
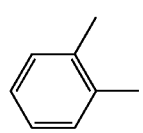

-continued (12-3)
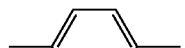

(12-4)
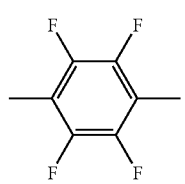

(12-5)
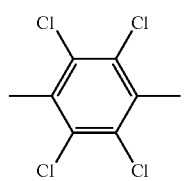

(12-6)
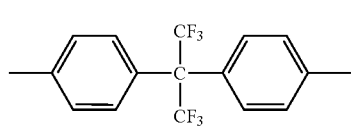

(12-7)
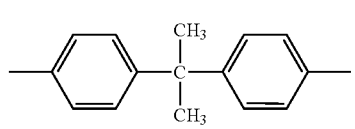

(12-8)
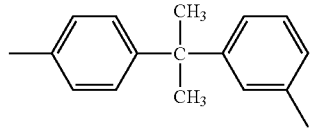

(12-9)
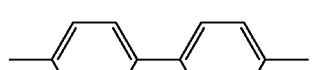

(12-10)

(12-11)
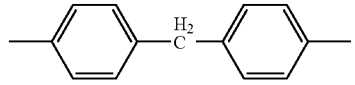

(12-12)
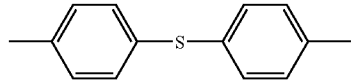

(12-13)
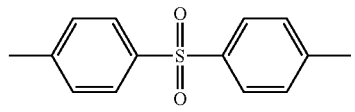

(12-14)
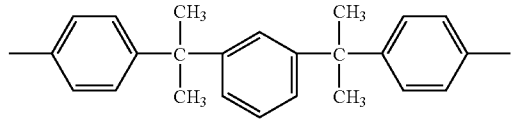

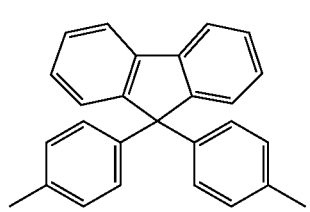

-continued

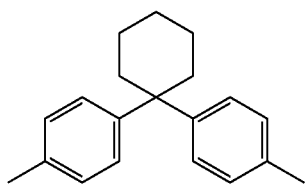
(12-15)

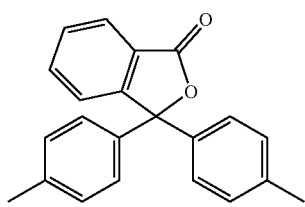
(12-16)

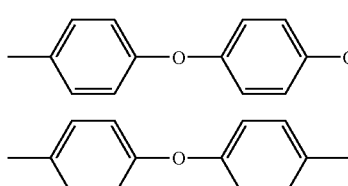
(12-17)

(12-18)

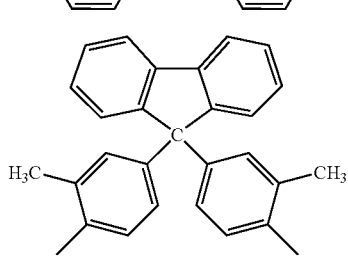
(12-19)

In the fluorine-containing ester compound of the present invention, it is preferred that a structure of $R^1$ in the above formula (3) is any of the above (12-6) or (12-18). That is, the fluorine-containing ester compound of the present invention is preferably represented by the following formula (4) or (5):

(4)

(5)

in the formula, m and n are same or different and each represents the number of fluorine atom bonded to a benzene ring and is an integer of 0 to 5 and m+n is 1 or more.

When the fluorine-containing ester compound has such a structure, the effect of the present invention will be exerted more effectively.

A method of producing the fluorine-containing ester compound represented by the above formula (3) is not particularly limited, but a method of producing the fluorine-containing ester compound using fluorine-containing benzoyl chloride and a dihydroxy compound (diol compound) as materials is suitable. For example, when a fluorine-containing ester compound, in which five hydrogen atoms of a benzene ring is replaced with five fluorine atoms, is produced, a method comprising the step of synthesizing the fluorine-containing ester compound by reacting pentafluorobenzoyl chloride with the dihydroxy compound as shown in the following formula (13) is suitable.

(13)

In addition, in this reaction, two or more species of fluorine-containing benzoyl chlorides, which are different from each other in number of or locations of fluorine atoms bonded to a benzene ring as a raw material, may be used.

In a reaction represented by the above formula (13), it is preferred to appropriately set the ratio between the fluorine-containing benzoyl chloride and the dihydroxy compound, used as raw materials, from the viewpoint of the effective use of reaction materials and the improvement in product yield. And it is preferred to use the dihydroxy compound in an amount of 0.2 to 1.2 mol with respect to 1 mol of the fluorine-containing benzoyl chloride. It is more preferred to use the dihydroxy compound in an amount of 0.4 to 0.6 mol with respect to 1 mol of the fluorine-containing benzoyl chloride.

As a solvent in the above reaction of the formula (13), there can be used a solvent which can be used for synthesizing the fluorine-containing compound represented by the above formula (1). These solvents may be used alone or in combination of two or more species. Among these solvents, halogenated hydrocarbons such as chloroform, methylene chloride, carbon tetrachloride, chloroethane, dichloroethane, trichloroethane, tetrachloroethane and the like are preferred. As an amount of a solvent, an amount capable of allowing the above reaction to proceed efficiently may be employed, but it is preferred to employ such an amount that the concentration of the fluorine-containing benzoyl chloride in a solvent is 0.1 to 50% by mass. It is more preferred to employ such an amount that the concentration of the fluorine-containing benzoyl chloride in a solvent is 1 to 30% by mass.

As reaction conditions of a reaction of the above formula (13), conditions capable of allowing the above reaction to proceed efficiently may be employed, and as a reaction temperature, it is preferred to employ a temperature of −50 to 150° C. and more preferred to employ a temperature of −5 to 50° C. And, as a reaction time, it is preferred to employ 0.01 to 20 hours and more preferably 0.5 to 3 hours. Further, the above reaction may be carried out under either reduced pressure, normal pressure or pressurization, but the reaction is preferably carried out under normal pressure considering an aspect of facilities and the like.

The present invention also provides a fluorine-containing aryl ester polymer which comprises a repeating unit represented by the following formula (6):

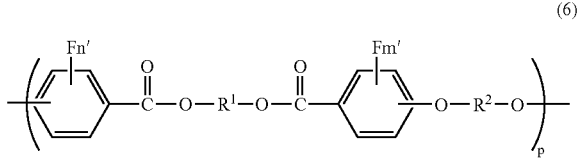

(6)

in the formula, m' and n' are same or different and each represents the number of fluorine atoms bonded to a benzene ring and is an integer of 0 to 4 and m'+n' is an integer of 1 or more; $R^1$ and $R^2$ are same or different and each represents a divalent organic group having 1 to 150 carbon atoms; and p represents a polymerization degree.

The fluorine-containing aryl ester polymer of the present invention may other repeating units as long as the polymer essentially comprises the repeating unit represented by the above-mentioned formula (16) and it is more preferable that the repeating unit represented by the above-mentioned formula (16) is a main component of the repeating units composing the fluorine-containing aryl ester polymer. In the fluorine-containing aryl ester polymer of the present invention the repeating unit represented by the formula (16) may be same or different. In the case where the polymer is composed of different repeating units, the polymer may be in form of a block or random.

in the fluorine-containing aryl ester polymer of the present invention, some or all of four hydrogen atoms of the fluorine atom-containing benzene ring are replaced with fluorine atoms or the hydrogen atoms of the benzene ring may be replaced with other substituent groups such as halogen atoms other than fluorine atoms and alkyl chain-containing substituent groups. Accordingly, the total of hydrogen atoms, fluorine atoms, halogen atoms other than fluorine atom, and other substituent groups is 4 in benzene ring. $R^1$ and $R^2$ are same or different and each represents a divalent organic group of 1 to 150 carbon atoms. $R^1$ and $R^2$ are more preferably the same as $R^1$ in the above-mentioned formula (3).

In the fluorine-containing aryl ester polymer of the present invention, the structure represented by $R^1$ is preferable to have a structure represented by the formula (12-6) or (12-18). That is, the fluorine-containing aryl ester polymer of the present invention is preferable to comprise a repeating unit represented by the following formula (7):

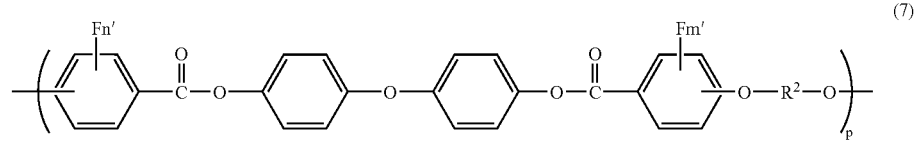

(7)

in the formula, m' and n' are same or different and each represents the number of fluorine atom bonded to a benzene ring and is an integer of 0 to 4; m'+n' is 1 or more; $R^2$ represents a divalent organic group having 1 to 150 carbon atoms; and p represents a polymerization degree, and/or a repeating unit represented by the formula (8):

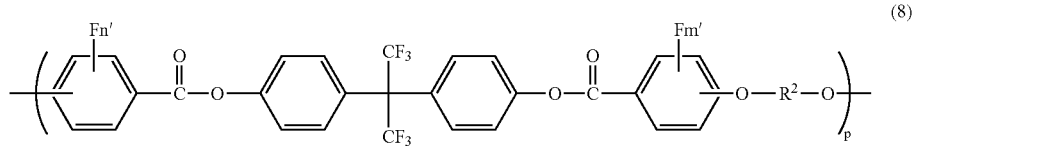

in the formula, m' and n' are same or different and each represents the number of fluorine atom bonded to a benzene ring and is an integer of 0 to 4; m'+n' is 1 or more; $R^2$ represents a divalent organic group having 1 to 150 carbon atoms; and p represents a polymerization degree. When the fluorine-containing aryl ester polymer has such a structure, the effects of the present invention may be more efficiently exhibited.

The polymerization degree represented by p is preferably in a range of 1 to 5000 and more preferably in a range of 1 to 500.

A method of producing the fluorine-containing aryl ester polymer of the present invention comprising a repeating unit represented by the above formula (6) is not particularly limited, but a method comprising the step of polymerizing the fluorine-containing ester compound described above with a dihydroxy compound, is preferred. And, this step is preferably performed in the presence of a basic catalyst from the viewpoint of a reaction efficiency.

That is, the fluorine-containing aryl ester polymer represented by the above formula (6) is preferably produced by a method comprising the step of polymerizing the fluorine-containing ester compound represented by the following formula (3):

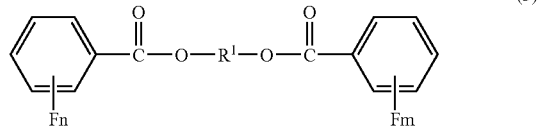

in the formula, m and n are same or different and each represents the number of fluorine atoms bonded to a benzene ring and is an integer of 0 to 5 and m+n is 1 or more; and $R^1$ represents a divalent organic group having 1 to 150 carbon atoms, with the dihydroxy compound represented by the following formula (9):

HO—$R^2$—OH  (9)

in the formula, $R^2$ represents a divalent organic group having 1 to 150 carbon atoms, in the presence of a basic catalyst, and such a method of producing is also one of the present invention.

Since the fluorine-containing ester compound of the present invention represented by the above formula (3) has high reactivity, when this fluorine-containing ester compound is used as a raw material to produce a polymer like the method of producing the above fluorine-containing aryl ester polymer, it is possible to employ various methods of polymerization such as homogeneous polymerization, interfacial polymerization and the like and it is possible to polymerize even under the conditions of 150° C. or lower which is lower than that of the conventional polymerization reaction using the fluorine-containing compound.

In the above method of producing the fluorine-containing aryl ester polymer, a portion of a structure (—O—$R^2$—O—) derived from a dihydroxy compound may be bonded to any of carbon atoms in an ortho position, a meta position and a para position to a carbon atom in the benzene ring bonded to an ester group, but it is preferably bonded to a carbon atom in an ortho position or a para position. And, if two or more portion of a structure derived from a dihydroxy compound are bonded to a benzene ring, a crosslinked structure may be formed, but when the polymer to be produced has a crosslinked structure, it gelates and therefore a compound having less crosslinked structure is preferred. In the above method of producing, since the tendency of generation of a crosslinked structure varies depending on a reaction temperature and a reaction time, species and concentration of a solvent and a basic catalyst to be used, and an order of material charge and a water content in a reaction system and the like, by optimizing these conditions, it becomes possible to suppress the generation of the crosslinked structure.

In a polycondensation reaction in the above method of producing the fluorine-containing aryl ester polymer, it is preferred to appropriately set the ratio between the dihydroxy compound and the fluorine-containing ester compound, used as raw materials, from the viewpoint of the effective use of a reaction material and the improvement in product yield. And it is preferred to use the dihydroxy compound in an amount of 0.8 to 1.2 mol with respect to 1 mol of the fluorine-containing ester compound. It is more preferred to use the dihydroxy compound in an amount of 0.9 to 1.1 mol with respect to 1 mol of the fluorine-containing ester compound.

As a reaction temperature of the polycondensation reaction in the above method of producing the fluorine-containing aryl ester polymer, it is preferred to employ a temperature of 0 to 100° C. and more preferred to employ a temperature of 10 to 80° C. And, as a reaction time, it is preferred to employ 1 to 40 hours and more preferably 1 to 30 hours. Furthermore, the above reaction may be carried out under either reduced pressure, normal pressure or pressurization, but the reaction is preferably carried out under normal pressure considering an aspect of facilities and the like.

In the polycondensation reaction in the above method of producing the fluorine-containing aryl ester polymer, various solvents can be used because of the high solubility of the fluorine-containing ester compound in a solvent and solvents which can be used for synthesizing the fluorine-containing compound represented by the above formula (1) can be used. These solvents may be used alone or in combination of two or more species. Among these solvents, acetone, acetonitrile, methyl isobutyl ketone (MIBK), methyl ethyl ketone (MEK), N-methyl-2-pyrrolidone (NMP), dimethylformamide (DMF), dimethyl sulfoxide (DMSO) and dimethylacetamide (DMAc) are preferred. As an amount of a solvent, an amount capable of allowing the above reaction to proceed efficiently may be employed, but it is preferred to employ such an amount that the concentration of the fluorine-containing ester compound in a solvent is 1 to 50% by mass and more preferably such an amount that the concentration is 1 to 30% by mass.

As a basic compound used in the above polycondensation reaction in the method of producing the fluorine-containing aryl ester polymer, a compound, which acts to accelerate the polycondensation reaction by catching the hydrogen fluoride produced by the polycondensation reaction and further has an action that changes the dihydroxy compound like the above to a more reactive anion, is suitable. And as such a basic compound, one or two or more species of, for example, calcium carbonate, calcium hydroxide, potassium fluoride, tributylamine, pyridine, potassium carbonate, lithium carbonate, potassium hydroxide, triethylamine and the like are suitable. An amount of such a basic compound to be used is preferably 0.5 to 20 mol with respect to 1 mol of the fluorine-containing ester compound to be used. It is more preferably 0.8 to 10 mol.

After the completion of the above polycondensation reaction, a solvent in a reaction solution is removed by evaporation or the like and distillate is washed as required, and thereby the fluorine-containing aryl ester polymer having a repeating unit represented by the above formula (6) is obtained. Further, the fluorine-containing aryl ester polymer can also be obtained by precipitating it as solid matter through mixing the reaction solution into a solvent, in which the solubility of this aryl ester polymer is low, and separating the precipitate through filtration.

Since the fluorine-containing aryl ester polymer of the present invention has excellent solubility in solvents, the polymer may be used in form of various formed bodies such as film-like and fibrous forms. A formed body comprising the fluorine-containing aryl ester polymer of the present invention is also one of the present invention.

The formed body of the present invention may comprise other components as long as it comprises the fluorine-containing aryl ester polymer essentially of the present invention. In the case where other components are added, the ratio of the fluorine-containing aryl ester polymer is preferably 30% by weight or more and more preferably 50% by weight or more in 100% by weight of the formed body.

The formed body of the present invention may comprise the above-mentioned fluorine-containing ester compound of the present invention. That is, the formed body of the present invention may comprise a mixture of the fluorine-containing aryl ester polymer and the fluorine-containing ester compound. In the case where the formed body of the present invention comprises a mixture of the fluorine-containing aryl ester polymer and the fluorine-containing ester compound, the content ratio of both is not particularly limited and it is preferable that the ratio of the total in both of the polymer and the compound is 30% by weight or more and more preferably 50% by weight or more in 100% by weight of the formed body.

In the case where the formed body which comprises the fluorine-containing aryl ester polymer of the present invention is used as a film-like formed body such as a film or a sheet, the thickness is preferably 0.1 µm or more and more preferably 1000 µm or less. In the case where it is used as a fibrous formed body, the diameter is preferably 5 µm or more and 10000 µm or less.

Examples of formed bodies in other forms include formed bodies with pallet-like shapes, sheet-like shapes such as a flat sheet and a corrugated sheet, and pipe-like shapes; and irregular formed bodies with semi-circular shapes, L-shapes, T-shapes, U-shapes, and hill-like shapes. Examples of a forming method of the above-mentioned formed body(formed product) may preferably include methods of injection molding, extrusion molding, vacuum molding, blow molding, heat molding, compaction molding, calendar molding, powder molding, foaming molding, layer molding, solvent casting, spin coating and the like.

The formed body containing the fluorine-containing aryl ester polymer of the present invention has a high molding processability attributed to the excellent solubility in solvents as described above and in addition to that, the formed body is excellent in heat resistance, low water absorption property, transparency, weathering resistance, and electric property, and therefore the formed body may preferably be used in various fields as super engineering plastic; insulating material for high frequency electronic part and high frequency wiring board; electronic information material and precision machine material used for coating agent, low dielectric film, insulating coating film on surface wiring of printed circuit board, semiconductor element, and coating material of lead wire; and optical communication and recording material such as optical film used for substrate and optical compensation layer and the like, optical waveguide, communication material, optical fiber, optical recording, and liquid crystal display, and substrate for display. The formed body comprising the fluorine-containing aryl ester polymer of the present invention may be used in various forms as described above and in various fields and among them, it is preferable to be used as a film.

The fluorine-containing ester compound and fluorine-containing aryl ester polymer of the present invention also may be used as an additive for resin.

When the fluorine-containing ester compound of the present invention and/or the fluorine-containing aryl ester polymer are added to resin, the water absorption property of the resin is efficiently lowered and a resin composition preferably usable in field such as optical communication, optical waveguide, optical recording, liquid crystal display in which resin material with low water absorption property are required may be produced.

A material for optical and electronic parts of the present invention is produced by using a polymer having a fluorine-containing oxadiazole structural unit represented by the following formula (10):

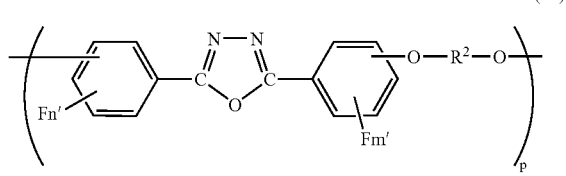

(10)

in the formula, m' and n' are same or different and each represents the number of fluorine atoms bonded to a benzene ring and is an integer of 0 to 4 and m'+n' is an integer of 1 or more; $R^2$ represents a divalent organic group having 1 to 150 carbon atoms; and p represents a polymerization degree. That the above-mentioned material is produced by using a polymer having a structure unit of fluorine-containing oxadiazole (herein after, referred to as a fluorine-containing oxadiazole polymer) means that the material for optical and electronic parts contains the fluorine-containing oxadiazole polymer, namely, that the fluorine-containing oxadiazole polymer is a component composing the material for optical and electronic parts.

The material for optical and electronic parts of the present invention may contain other components as long as the fluorine-containing oxadiazole polymer is contained. For example, the fluorine-containing oxadiazole compound mentioned below may be contained. That is, the material for optical and electronic parts of the present invention may be mixture of the fluorine-containing oxadiazole polymer and the fluorine-containing oxadiazole compound. In the case where the materials for optical and electronic parts are a mixture of the fluorine-containing oxadiazole polymer and the fluorine-containing oxadiazole compound, the mixing ratio of both of the polymer and the compound is not especially limited.

The fluorine-containing oxadiazole polymer to be used for the material for optical and electronic parts of the present invention may comprise other repeating units as long as the repeating unit represented by the above-mentioned formula (10) is essentially comprised, and the repeating unit represented by the above-mentioned formula (10) is preferably a main component of the repeating unit composing the fluorine-containing oxadiazole polymer. Additionally, with respect to the fluorine-containing oxadiazole polymer of the present invention, the structure of the repeating unit represented by the above-mentioned formula (10) may be same or different, and in the case where the polymer is composed of different repeating units, the polymer may be in form of block or random polymer.

With respect to the repeating unit represented by the above-mentioned formula (10), the (—O—R$^2$—O—) part may be bonded to any of carbons at o-, m- or p-position relative to the carbon bonded to the oxadiazole ring of the benzene ring, but the part is preferable to be bonded to the carbon at o- or p-position. In the fluorine-containing oxadiazole polymer of the present invention, some or all of four hydrogen atoms of the fluorine atom-containing benzene ring are replaced with fluorine atoms or the hydrogen atoms of the benzene ring may be replaced with substituent groups other than fluorine atoms. Accordingly, the total of hydrogen atoms, fluorine atoms, and other substituent groups other than fluorine atom in one benzene ring is 4. R$^2$ represents a divalent organic group of 1 to 150 carbon atoms and the divalent organic group is more preferably an organic group of 1 to 50 carbon atoms. A group represented by the above-mentioned formulae (11-1) to (11-18) are more preferable.

As a substituent group in Y$^1$, Y$^2$, Y$^3$, and Y$^4$ in the above-mentioned formulae (11-1) to (11-18), preferable examples are alkyl and alkoxy groups, which each may contain a substituent group, and halogen atoms. More preferable examples are alkyl and alkoxy groups of 1 to 30 carbon atoms, which may contain a substituent group, and halogen atoms. R$^2$ is preferably a group represented by the above-mentioned formulae (12-1) to (12-19).

The above-mentioned the polymerization degree represented by p is preferably in a range of 1 to 5000 and more preferably in a range of 1 to 500.

A method of producing the fluorine-containing oxadiazole polymer represented by the above formula (10) is not particularly limited and includes a method (production method 1) by obtaining a polymer from polycondensation reaction of fluorine-containing dibenzoylhydrazide and a dihydroxy compound (diol compound) and then cyclizing the resulting polymer, and a method (production method 2) by cyclizing fluorine-containing dibenzoylhydrazide, which is a product of the reaction of fluorine-containing benzoyl chloride and hydrazine, to form fluorine-containing oxadiazole compound and then polycondensing the resulting fluorine-containing oxadiazole compound with a dihydroxy compound and the like. Of these two production methods, the production method 2 is preferred from the viewpoint of a production efficiency of copolymerization and the like. When diperfluorobenzoylhydrazide (10F-BH) is used as dibenzoylhydrazide, reaction formulae of the production methods 1 and 2 are as the following formulae (14) and (15), respectively.

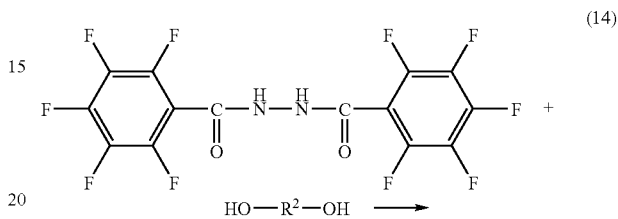

(14)

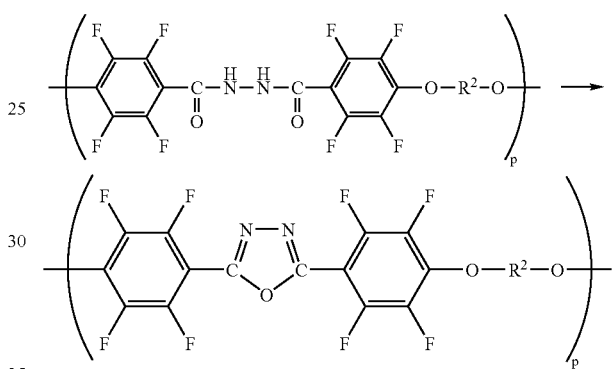

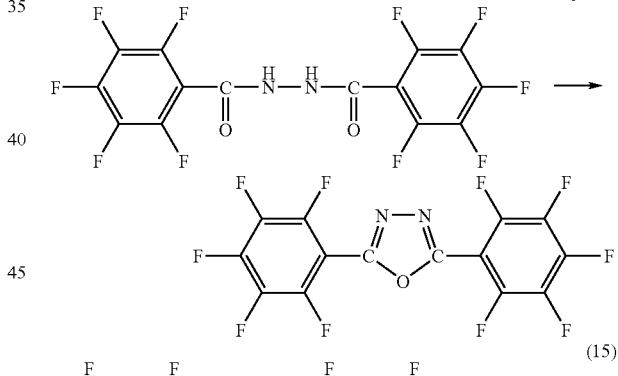

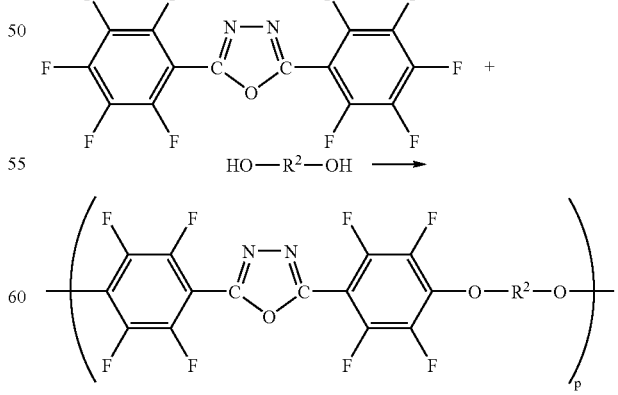

(15)

The fluorine-containing oxadiazole compound used in the above production method 2 has high reactivity because a oxadiazole ring exists between two benzene rings, and therefore when such fluorine-containing oxadiazole compound is used as a raw material to produce a polymer, it is possible to employ various methods of polymerization such as homogeneous polymerization, interfacial polymerization and the like. And, it is possible to polymerize at lower temperature than the conventional fluorine-containing compound.

When a polymer is produced by the above production method 2, it is preferred to use a oxadiazole compound having a benzene ring to which more fluorine atoms are bonded as a fluorine-containing oxadiazole compound and a oxadiazole compound having a benzene ring to which 3 to 5 fluorine atoms are bonded is preferred. It becomes possible to allow a polymerization reaction to proceed at lower temperature as number of fluorine atoms increases. An oxadiazole compound having a benzene ring to which 5 fluorine atoms are bonded is more preferred. By selecting appropriately the number of fluorine atoms which the fluorine-containing oxadiazole compound has and a structure of $R^2$ in the above formula (10) like this, it becomes possible to produce a highly fluorinated polymer in which many of hydrogen atoms of a benzene ring contained in a structure of copolymer are replaced with fluorine atoms or a polymer in which all of hydrogen atoms of a benzene ring contained in a structure of copolymer are replaced with fluorine atoms.

In a polycondensation reaction in the above production method 2, it is preferred to appropriately set the ratio between the dihydroxy compound and the fluorine-containing oxadiazole compound used as raw materials, from the viewpoint of the effective use of a reaction material and the improvement in product yield. And it is preferred to use the dihydroxy compound in an amount of 0.8 to 1.2 mol with respect to 1 mol of the fluorine-containing oxadiazole compound. It is more preferred to use the dihydroxy compound in an amount of 0.9 to 1.1 mol with respect to 1 mol of the fluorine-containing oxadiazole compound.

As a reaction temperature of the polycondensation reaction in the above production method 2, it is preferred to employ a temperature of 0 to 100° C. and more preferred to employ a temperature of 10 to 70° C. And, as a reaction time, it is preferred to employ 1 to 40 hours and more preferably 1 to 30 hours. Further, the above reaction may be carried out under either reduced pressure, normal pressure or pressurization, but the reaction is preferably carried out under normal pressure considering an aspect of facilities and the like.

In the polycondensation reaction in the above production method 2, various solvents can be used because of the high solubility of the fluorine-containing oxadiazole compound in a solvent and solvents same as that used for the synthesis of fluorine-containing compound represented by above formula (1) can be used. These solvents may be used alone or in combination of two or more species. Among these solvents, acetonitrile, methyl isobutyl ketone (MIBK), N-methyl-2-pyrrolidone (NMP), dimethylformamide (DMF), dimethyl sulfoxide (DMSO) dimethyl acetamide (DMAc) and methyl ethyl ketone (MEK) are preferred. As an amount of a solvent, an amount capable of allowing the above reaction to proceed efficiently may be employed, but it is preferred to employ such an amount that the concentration of the fluorine-containing oxadiazole compound in a solvent is 1 to 50% by mass and more preferably such an amount that the concentration is 10 to 40% by mass.

The polycondensation reaction in the above production method 2 is preferably carried out in the presence of a basic compound. As the basic compound, a compound, which acts to accelerate the polycondensation reaction by catching the hydrogen fluoride produced by the polycondensation reaction and further has an action that changes the dihydroxy compound like the above to a more reactive anion, is suitable, and one species or two or more species of, for example, potassium carbonate, lithium carbonate, potassium hydroxide and the like are suitable. An amount of such a basic compound to be used is preferably 0.5 to 10 mol with respect to 1 mol of the fluorine-containing oxadiazole compound to be used. It is more preferably 0.8 to 2 mol.

After the completion of the above polycondensation reaction, a solvent in a reaction solution is removed by evaporation or the like and distillate is washed as required, and thereby the fluorine-containing oxadiazole polymer having a repeating unit represented by the above formula (10) is obtained. Further, the fluorine-containing oxadiazole polymer can also be obtained by precipitating it as solid matter through mixing the reaction solution into a solvent, in which the solubility of this polymer is low, and separating the precipitate through filtration.

The material for optical and electronic parts of the present invention can be formed in a film-like form or can be used as a coating agent attributed to excellent solubility of the fluorine-containing oxadiazole polymer in solvents. In the case the material for optical and electronic parts of the present invention is used in form of a film, the thickness is preferably 0.1 µm or more and 1000 µm or less.

The film-like formed product made of the material for optical and electronic parts of the present invention is not only excellent in heat resistance but also in transparency and the film-like formed product is provided with high transmittance by properly selecting the structure and the like of the fluorine-containing oxadiazole polymer.

The material for optical and electronic parts of the present invention also may be used in form of fibrous formed products and various formed bodies.

With respect to the above-mentioned formed product, the fiber means a fibrous formed product and preferably has a diameter of 5 µm or more and 10000 µm or less. The formed body is a formed product having a predetermined formed shape and examples thereof may include formed bodies with pallet-like shapes, sheet-like shapes such as a flat sheet and a corrugated sheet, and pipe-like shapes; and irregular formed bodies with semi-circular shapes, L-shapes, T-shapes, U-shapes, and hill-like shapes.

Examples of a forming method of the above-mentioned formed product may preferably include methods of injection molding, extrusion molding, vacuum molding, blow molding, heat molding, compaction molding, calendar molding, powder molding, foaming molding, layer molding, solvent casting, spin coating and the like.

Since the fluorine-containing aryl ester polymer of the present invention has the high solubility in a solvent, it can be formed into formed body having various shapes such as film, fiber, etc. to be used. The formed body containing the fluorine-containing aryl ester polymer of the present invention has a high molding processability attributed to the excellent solubility in solvents as described above and in addition to that, the formed body is excellent in heat resistance, low water absorption property, transparency, weathering resistance, and electric property, and therefore the formed body may preferably be used in various fields as super engineering plastic; insulating material for high frequency electronic part and high frequency wiring board; electronic information material and precision machine material used for coating agent, low dielectric film, insulating coating film on surface wiring of printed circuit board, semiconductor element, coating material of lead wire, and adhesive; and optical communication and recording material such as optical film used for substrate and optical compensation layer and the like, optical waveguide, communication material, optical fiber, optical recording, and liquid crystal display, and substrate for display.

The fluorine-containing compound of the present invention represented by the formula (1), the fluorine-containing ester compound the present invention represented by the formula (3), and the fluorine-containing aryl ester polymer the present invention containing a repeating unit represented by the formula (6) can be employed as additives for resin. When the fluorine-containing ester compound and/or the fluorine-containing aryl ester polymer of the present invention is added to resin, it become possible to effectively make the resin low in moisture absorption and to change the resin to a resin composition which is suitably used also in fields, such as optical communication, an optical waveguide, optical recording and a liquid crystal display, where a resin material of low moisture absorption property is required. Such a resin composition can be used, for example, for lens such as an optical pickup lens, an fθ lens for laser beam printer, a lens for glass, a camera lens, a video camera lens, and a lamp lens; disk such as a video disk, an audio disk, and a re-writable disk for computer; and optical transmission material such as a plastic optical fiber (POF), an optical connector, and a photoconductor. And, this resin composition can be suitably used as materials for electronic information and materials for precision instruments and can be used, for example, for insulating material for high frequency electronic part and high frequency wiring board; coating agent, low dielectric film, insulating coating film on surface wiring of printed circuit board, semiconductor element, coating material of lead wire.

The material for optical and electronic parts comprising the polymer having a fluorine-containing oxadiazole structure unit represented by the above-mentioned formula (10) may be used in various uses in the optical and electric part fields. Examples of optical uses may include optical communication and recording materials such as optical films used for substrates and optical compensation layer and the like, optical waveguides, materials for communication, optical fibers, optical recording, liquid crystal display and the like. Examples of electronic parts may include, high frequency electronic parts as insulating materials, high frequency wiring substrate, coating agents, low dielectric films, insulating coating films of surface wiring of printed circuit boards, coating materials of semiconductor devices and lead wires, and adhesives. In these uses, the material and the composition are provided with low water absorption property to result in improvement of reliability.

The fluorine-containing compound of the present invention represented by the formula (1) has the above-mentioned constitution and in the case where, for example, the compound is used as an additive for the transparent resin material, the compound can lower the water absorption property of the transparent resin material and provide water repellency to the transparent resin material without deteriorating the various properties such as transparency of the transparent resin. Furthermore, it is expected that addition of the fluorine-containing compound of the present invention to a resin may give the effect such as lowering the refractive index and dielectric constant of the resin, which are effects generally given by a compound containing fluorine atom.

And, the method of producing the fluorine-containing compound of the present invention having a specific structure is preferable method for producing effectively a fluorine-containing compound being suitable as such an additive for a transparent resin material.

And, since the fluorine-containing ester compound of the present invention represented by the formula (3) and the fluorine-containing aryl ester polymer of the present invention containing a repeating unit represented by the formula (6) has the above-mentioned constitution are excellent in low water absorption property and weathering resistance. The polymer is excellent in various properties such as heat resistance, weathering resistance, electric properties, and transparency, and therefore the fluorine-containing ester compound and fluorine-containing aryl ester polymer of the present invention may be preferably used in various fields such as an electronic information material, a precision machine material, and an optical material. Furthermore, addition of the fluorine-containing ester compound of the present invention represented by the formula (3) and the fluorine-containing aryl ester polymer of the present invention containing a repeating unit represented by the formula (6) to resin provides the resin with sufficiently lowered water absorption property and gives a transparent resin material preferably usable in fields such as optical communication, optical waveguide, optical recording, liquid crystal display in which the material having lowered water absorption is required.

In addition, the material for optical and electronic parts containing the polymer having a fluorine-containing oxadiazole structural unit represented by the formula (10) of the present invention has the above-mentioned constitution, and since the material for optical and electronic parts is excellent in the transparency, heat resistance, water repellency, and electrochemical properties and the like, and the fluorine-containing oxadiazole compound is also excellent in the solubility in solvents, the material may be used in various forms such as a film and a coating agent in optical and electronic part fields. Furthermore, since addition of the fluorine-containing oxadiazole compound to resin provides the resin with sufficiently lowered water absorption property, the fluorine-containing oxadiazole compound may be used preferably as an additive for resin.

BEST MODE FOR CARRYING OUT THE INVENTION

The present invention will, hereinafter, be described in more detail with reference to Examples, but the present invention is not be unduly limited to Examples.

SYNTHESIS EXAMPLE 1

Synthesis of heptadecafluorodecanoxytetrafluorobenzonitrile (17FD-TFBN)

Figure 2:
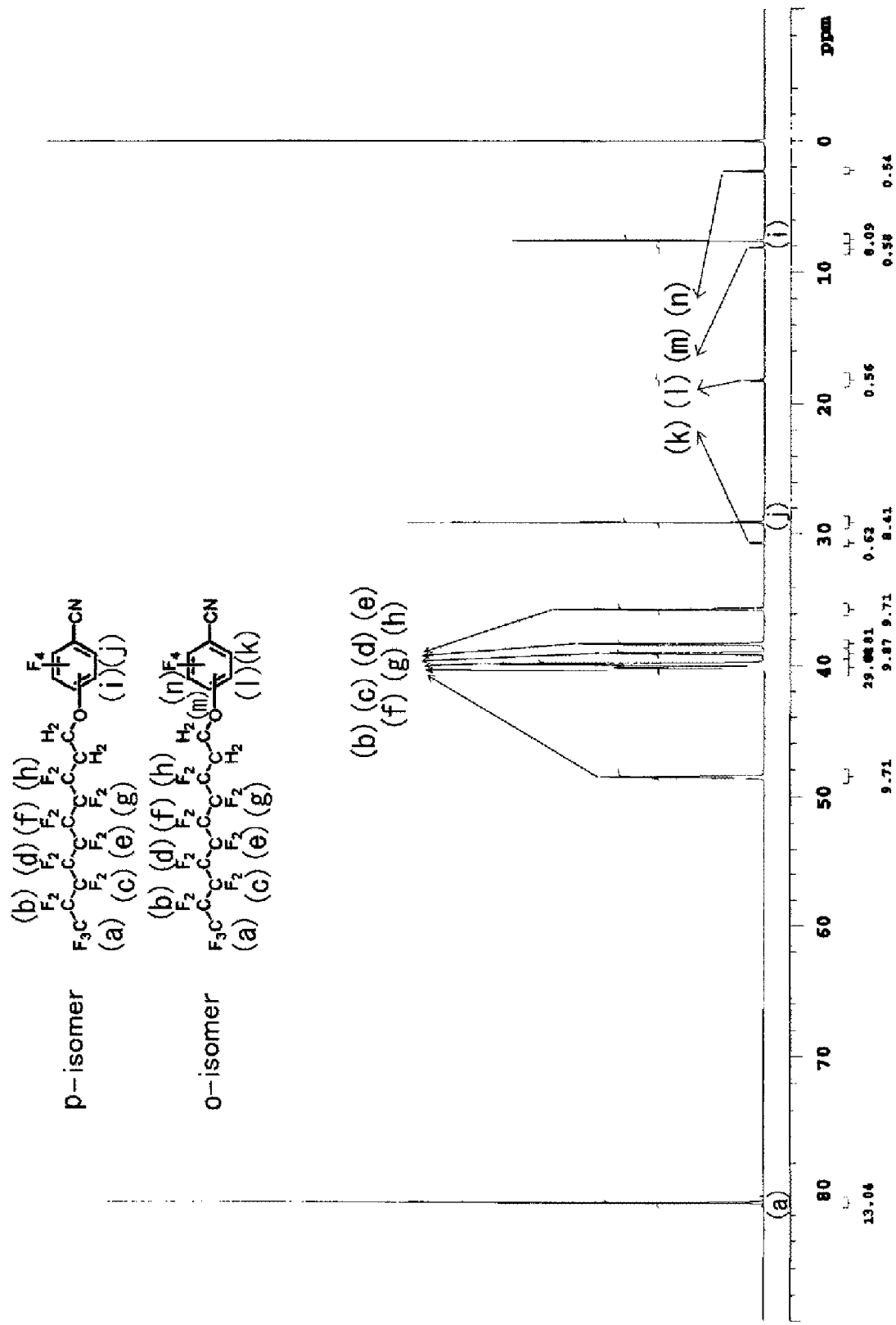
FIG. 2 shows a chart of $^{19}$F-NMR measurement of a mixture of heptadecafluorodecanoxy-2,3,5,6-tetrafluorobenzonitrile (p-isomer) and heptadecafluorodecanoxy-3,4,5,6-tetrafluorobenzonitrile (o-isomer), obtained in Synthetic Example 1 of the present invention.

Pentafluorobenzonitrile (PFBN) 5.66 g (29.31 mmol), heptadecafluorodecanol 9.28 g (19.99 mmol), potassium carbonate 1.45 g (10.49 mmol), and acetonitrile 50 g were all together charged into a reaction vessel. The reaction solution was heated at 70° C. for 24 hours and then cooled. On completion of the reaction, the precipitated salt was filtered and then the solvent was removed by distillation, the obtained crude product was distilled under reduced pressure in condition of 113 to 118° C./0.1 mmHg to obtain a white solid 8.92 g (yield 70%). The obtained product was mixture of heptadecafluorodecanoxy-2,3,5,6-tetrafluorobenzonitrile (p-isomer)/heptadecafluorodecanoxy-3,4,5,6-tetrafluorobenzonitrile (o-isomer)=87.7/12.3. The charts of $^1$H-NMR and $^{19}$F-NMR measurement of the obtained material are shown in FIG. 1 and FIG. 2. The ratios of p-isomer and o-isomer of the obtained compound was calculated by area ratio of peaks (i), (j) and (k), (l), (m), (n) in the chart of $^{19}$F-NMR shown in FIG. 2. $^1$H-NMR and $^{19}$F-NMR measurement were carried out with apparatus and conditions described later. The obtained 17FD-TFBN was evaluated for thermal property. The results are shown in Table 1. The measurement apparatus and conditions for the thermal property evaluation were described later.

TABLE 1

|  | 17FD-TFBN |
|---|---|
| Temperature at weight decrease of 2% by weight | 170° C. |

EXAMPLE 1 AND COMPARATIVE EXAMPLE 1

0.9 part of the substance 17FD-TFBN (mixture of p-isomer and o-isomer) produced in Synthesis Example 1 was dissolved in acrylic resin A (methyl methacrylate (MMA)/tert-butyl methacrylate (tBMA)/FM 108=60/30/10; solvent: methyl ethyl ketone (MEK)/toluene; solid matter 30%, FM 108: fluorine-containing methacrylic acid derivative, manufactured by Kyoeisha Chemical Co., Ltd.) 10 part to obtain a transparent resin material.

A film was produced by casting the material on PET by using the casting method and by separating the formed film. The film was not deteriorated in transparency and maintained excellent transparency. The film was measured for total luminous transmittance, haze, and water absorption ratio. The results are shown in Table 2. The measurement apparatuses and the conditions for total luminous transmittance, haze, and water absorption ratio measurements were described later.

TABLE 2

|  | Example 1 | Comparative Example 1 |
|---|---|---|
| Film | Film of acrylic resin A + 17FD-TFBN | Film of acrylic resin A |
| Total luminous trasmittance (%) | 93.6 | 93.6 |
| Haze (%) | 0.6 | 0.5 |
| Water absorption ratio (%) | 0.55 | 0.90 |

SYNTHESIS EXAMPLE 2

Synthesis of 4,4'-bis(2,3,4,5,6-pentafluorobenzoyloxy)diphenyl ether (BPDES)

4,4'-Hydoxydiphenyl ether 5.00 g (24.75 mmol), triethylamine 5.01 g (49.50 mmol), and dichloromethane 100 g were charged into a flask and kept at 10° C. in a water bath. Pentafluorobenzoyl chloride 11.41 g (49.50 mmol) and dichloromethane 20 g were added to a dropping funnel and dropwise added slowly to the flask.

Figure 3:
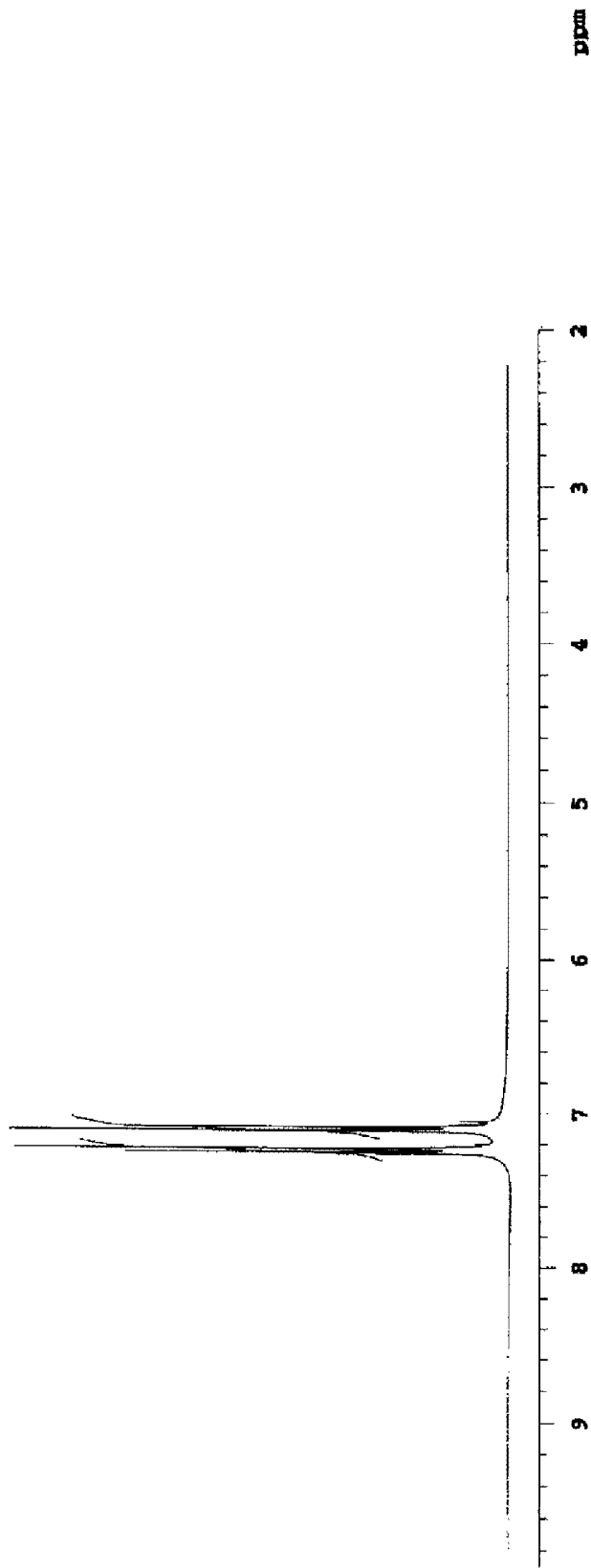
FIG. 3 shows a chart of $^1$H-NMR measurement of 4,4'-bis (2,3,4,5,6-pentafluorobenzoyloxy)diphenyl ether (BPDES) obtained in Synthetic Example 2 of the present invention.
Figure 4:
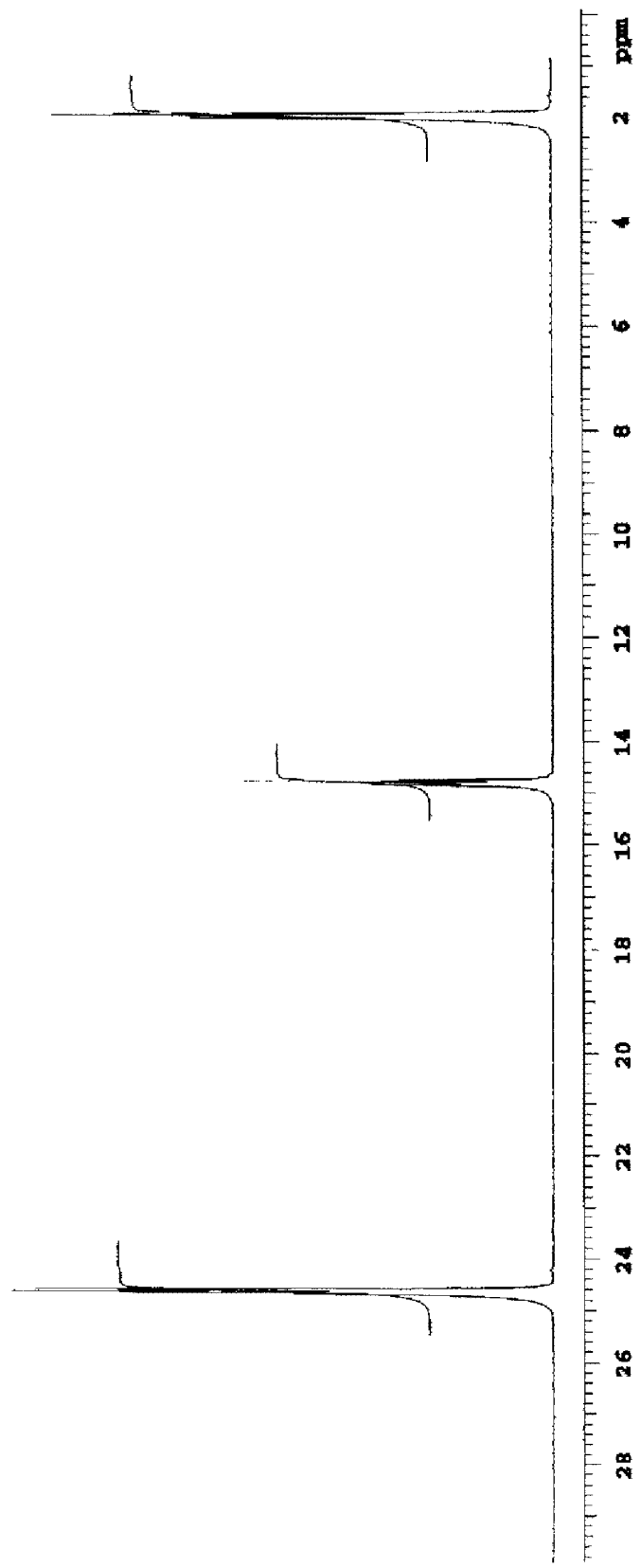
FIG. 4 shows a chart of $^{19}$F-NMR measurement of 4,4'-bis (2,3,4,5,6-pentafluorobenzoyloxy)diphenyl ether (BPDES) obtained in Synthetic Example 2 of the present invention.

On completion of the dropping addition, the water bath was taken out, the mixture was reacted at a room temperature for 3 hours. After the reaction, the mixture was added to water and the produced solid was recovered and recrystallized with methanol to obtain BPDES. The yield was 86.0% and the melting point Tm was 130° C. The charts of $^1$H-NMR and $^{19}$F-NMR measurement of the obtained BPDES are shown in FIG. 3 and FIG. 4. $^1$H-NMR and $^{19}$F-NMR measurement were carried out with apparatus and conditions described later.

SYNTHESIS EXAMPLE 3

Synthesis of 2,2-bis(pentafluorobenzoyloxyphenyl)-1,1,1,3,3,3-hexafluoropropane (BP6FBA)

Figure 5:
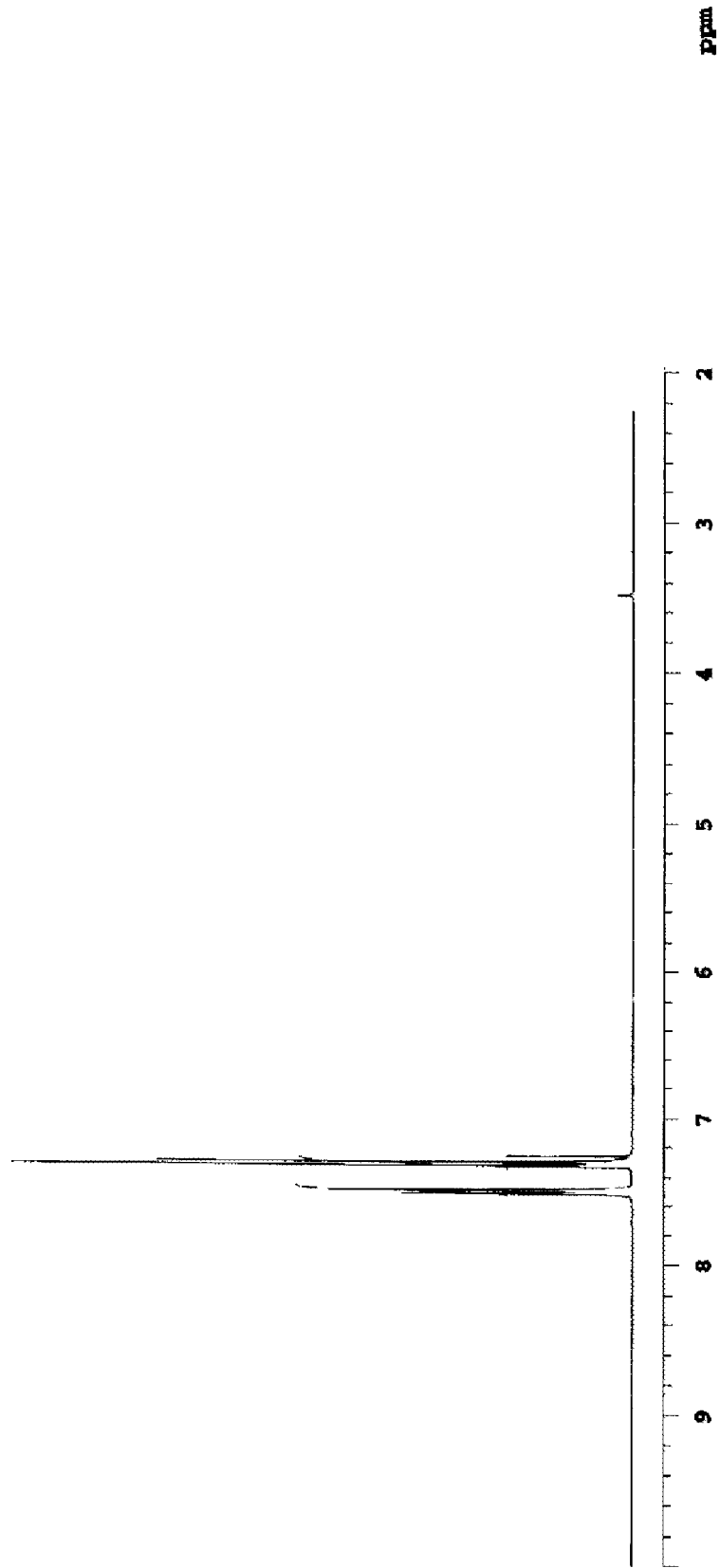
FIG. 5 shows a chart of $^1$H-NMR measurement of 2,2-bis (pentafluorobenzoyloxyphenyl)-1,1,1,3,3,3-hexafluoropropane (BP6FBA) obtained in Synthetic Example 3 of the present invention.
Figure 6:
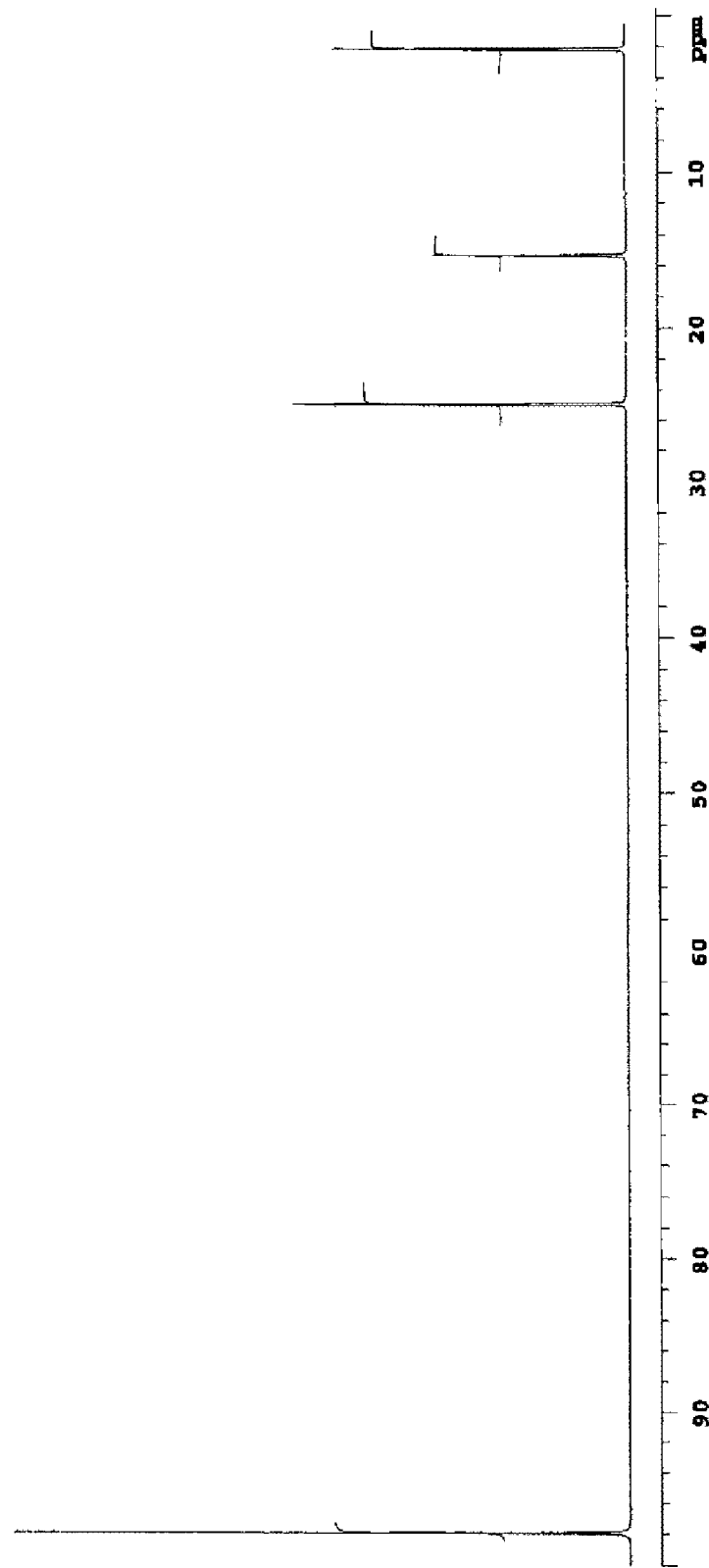
FIG. 6 shows a chart of $^{19}$F-NMR measurement of 2,2-bis (pentafluorobenzoyloxyphenyl)-1,1,1,3,3,3-hexafluoropropane (BP6FBA) obtained in Synthetic Example 3 of the present invention.

Using 2,2'-bis(4-hydoxyphenyl)hexafluoropropane 5.00 g (14.88 mmol), triethylamine 3.31 g (32.74 mmol), and pentafluorobenzoyl chloride 6.86 g (29.76 mmol) were used and synthesis was carried out in the same manner as in Synthesis example 1 to obtain BP6FBA. The yield was 80.7% and the melting point Tm was 119° C. The charts of $^1$H-NMR and $^{19}$F-NMR measurement of the obtained BP6FBA are shown in FIG. 5 and FIG. 6.

SYNTHESIS EXAMPLE 4

Synthesis of Polymer (BPDES-HF) Comprising BPDES and fluorene-9-bisphenol (HF)

Figure 7:
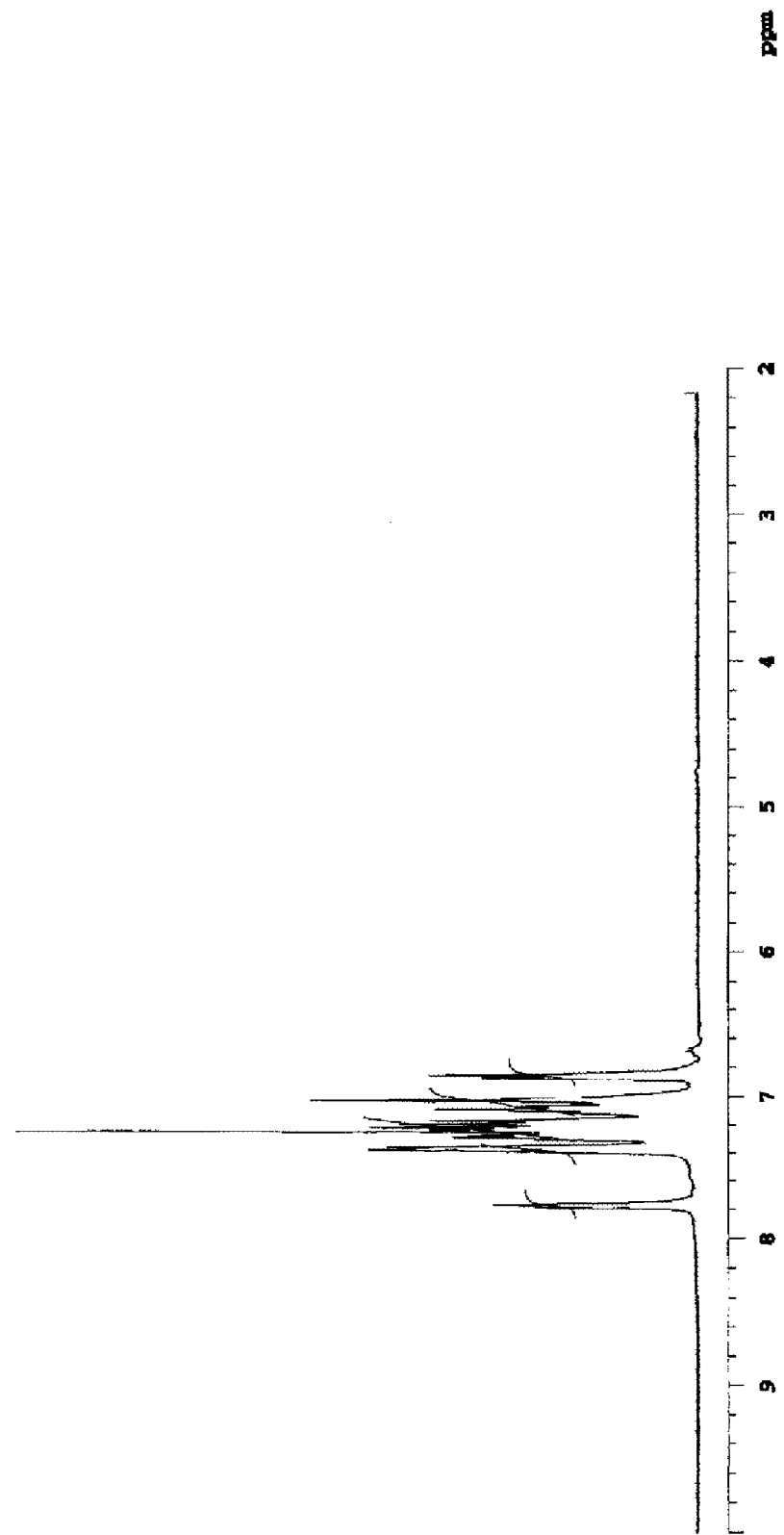
FIG. 7 shows a chart of $^1$H-NMR measurement of a polymer (BPDES-HF) obtained in Synthetic Example 4 of the present invention, consisting of BPDES and fluoren-9-bisphenol (HF).
Figure 8:
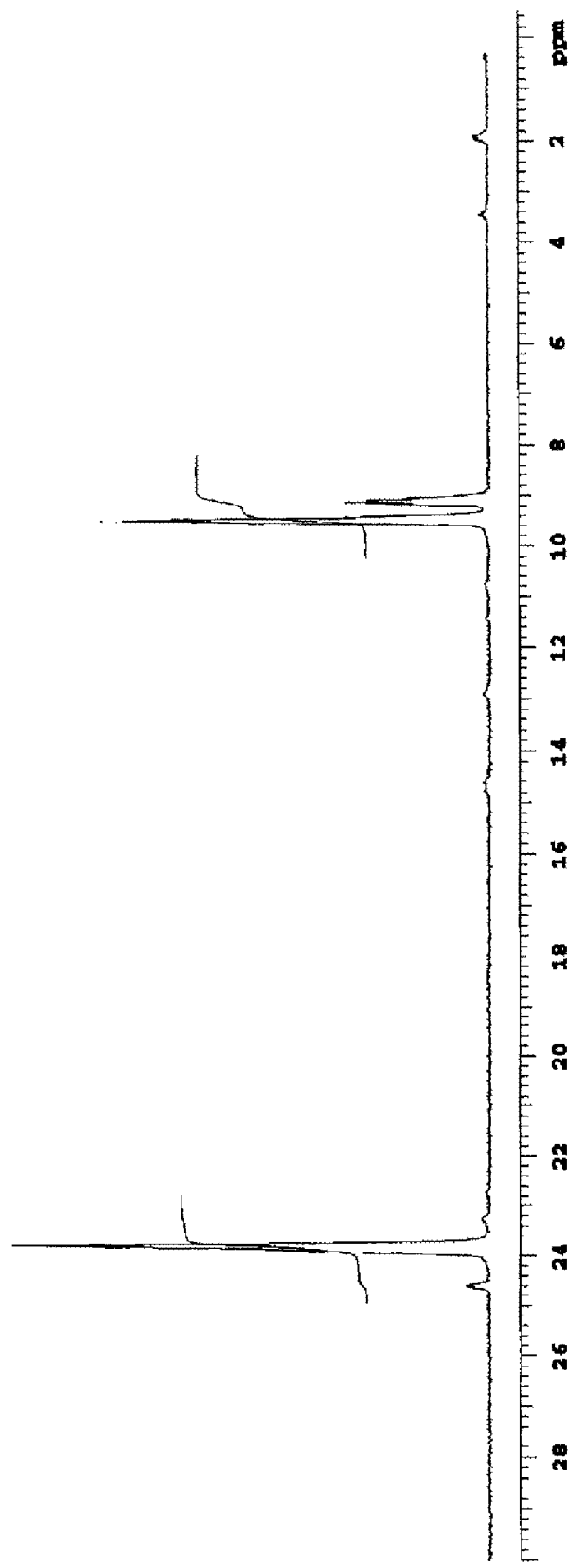
FIG. 8 shows a chart of $^{19}$F-NMR measurement of a polymer (BPDES-HF) obtained in Synthetic Example 4 of the present invention, consisting of BPDES and fluoren-9-bisphenol (HF).

BPDES 6.04 g (10.23 mmol), HF 3.59 g (10.23 mmol), potassium carbonate 7.07 g (51.16 mmol), a molecular sieve 10.00 g and MEK 100 g were charged and reacted at 75° C. for 2 hours. After that, the reaction solution was added to 0.5 L of deionized water to obtain a polymer (BPDES-HF). The yield of the polymer was 90%. The charts of $^1$H-NMR and $^{19}$F-NMR measurement of the obtained polymer are shown in FIG. 7 and FIG. 8. The produced polymer had a number average molecular weight of 15400. The polymer was also evaluated for thermal property and measured for transmittance, total luminous transmittance and evaluated for electric property. The results are shown in Tables 3, 4 and 5. The measurement of number average molecular weight, transmittance and total luminous transmittance and evaluation of electric property were carried out by the methods described later.

SYNTHESIS EXAMPLE 5

Synthesis of Polymer (BPDES-6FBA) comprising BPDES and hexafluorobisphenol A (6FBA)

Figure 9:
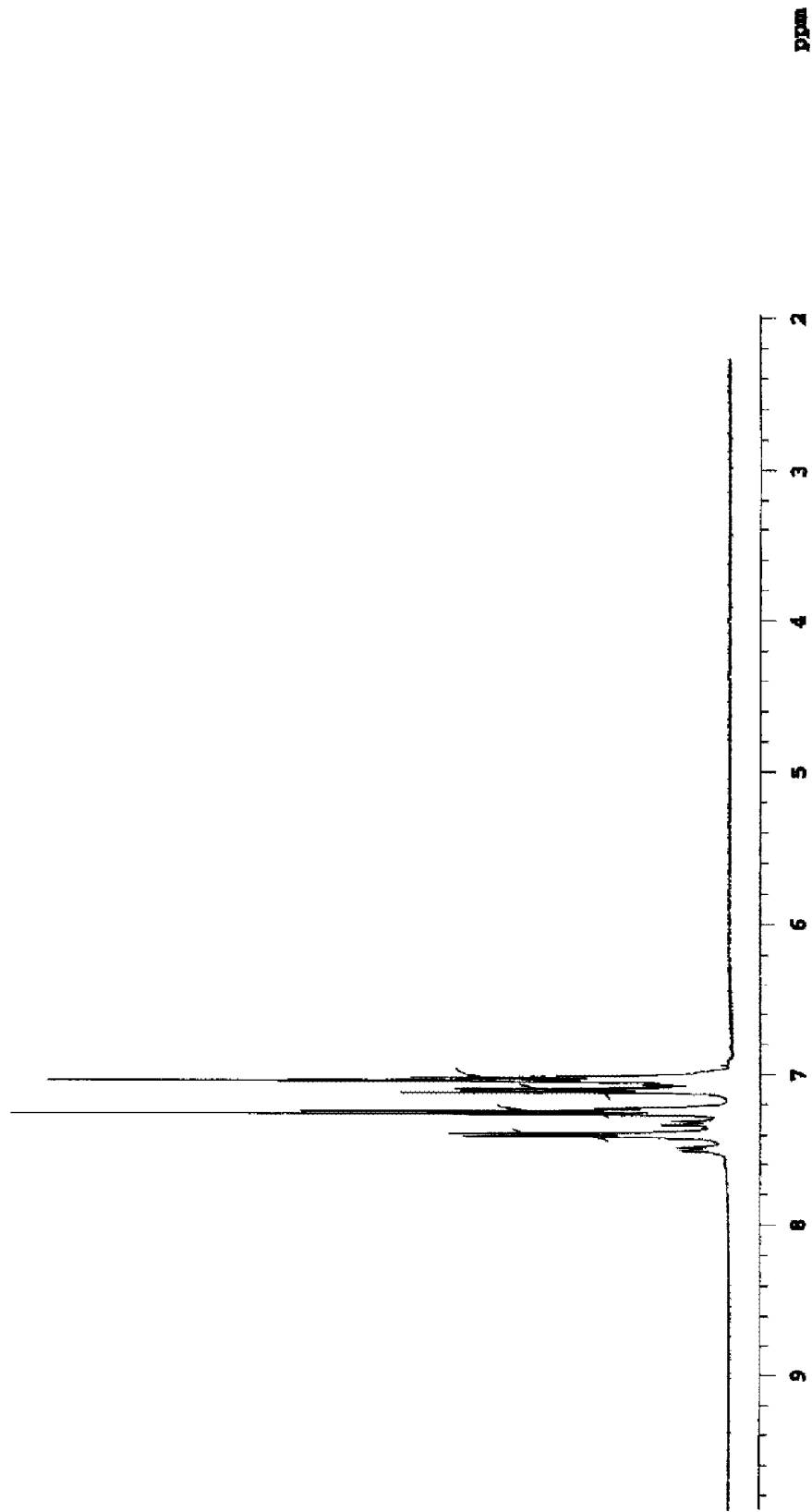
FIG. 9 shows a chart of $^1$H-NMR measurement of a polymer (BPDES-6FBA) obtained in Synthetic Example 5 of the present invention, consisting of BPDES and hexafluorobisphenol A (6FBA).
Figure 10:
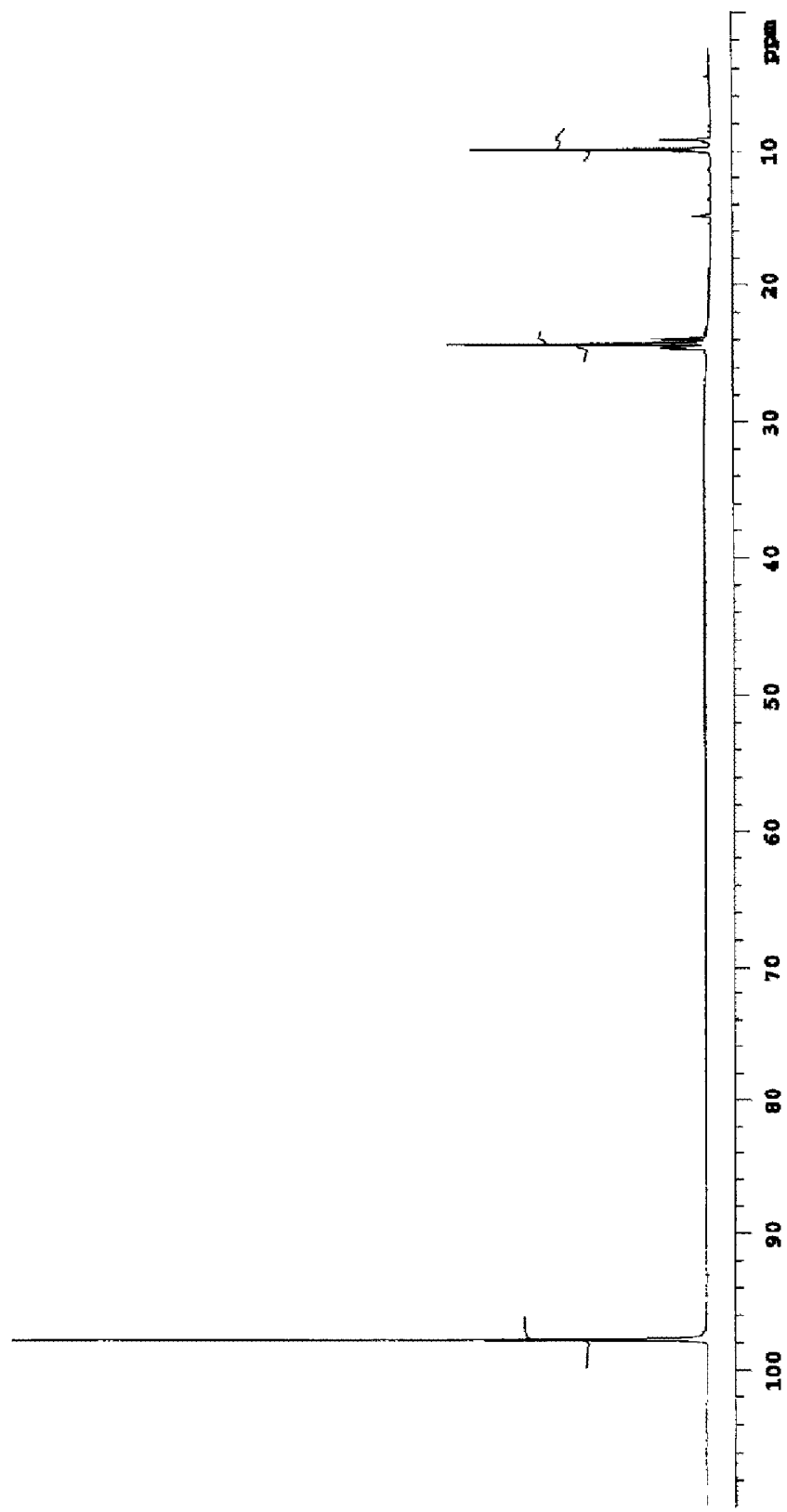
FIG. 10 shows a chart of $^{19}$F-NMR measurement of a polymer (BPDES-6FBA), obtained in Synthetic Example 5 of the present invention, consisting of BPDES and hexafluorobisphenol A (6FBA).

BPDES 3.00 g (5.08 mmol), 6FBA 1.70 g (5.08 mmol), potassium carbonate 3.51 g (25.40 mmol), a molecular sieve 10.00 g and methyl ethyl ketone (MEK) 100 g were charged and reacted at 75° C. for 2 hours. After that, the reaction solution was added to 0.5 L of deionized water to obtain a polymer. The yield of the polymer was 82%. The charts of $^1$H-NMR and $^{19}$F-NMR measurement of the obtained polymer are shown in FIG. 9 and FIG. 10. The produced polymer had a number average molecular weight 13000. The polymer was also evaluated for thermal property and measured for transmittance and total luminous transmittance and evaluated for electric property. The results are shown in Tables 3, 4 and 5.

SYNTHESIS EXAMPLE 6

Synthesis of Polymer (BP6FBA-6FBA) Comprising BP6FBA and 6FBA

Figure 11:
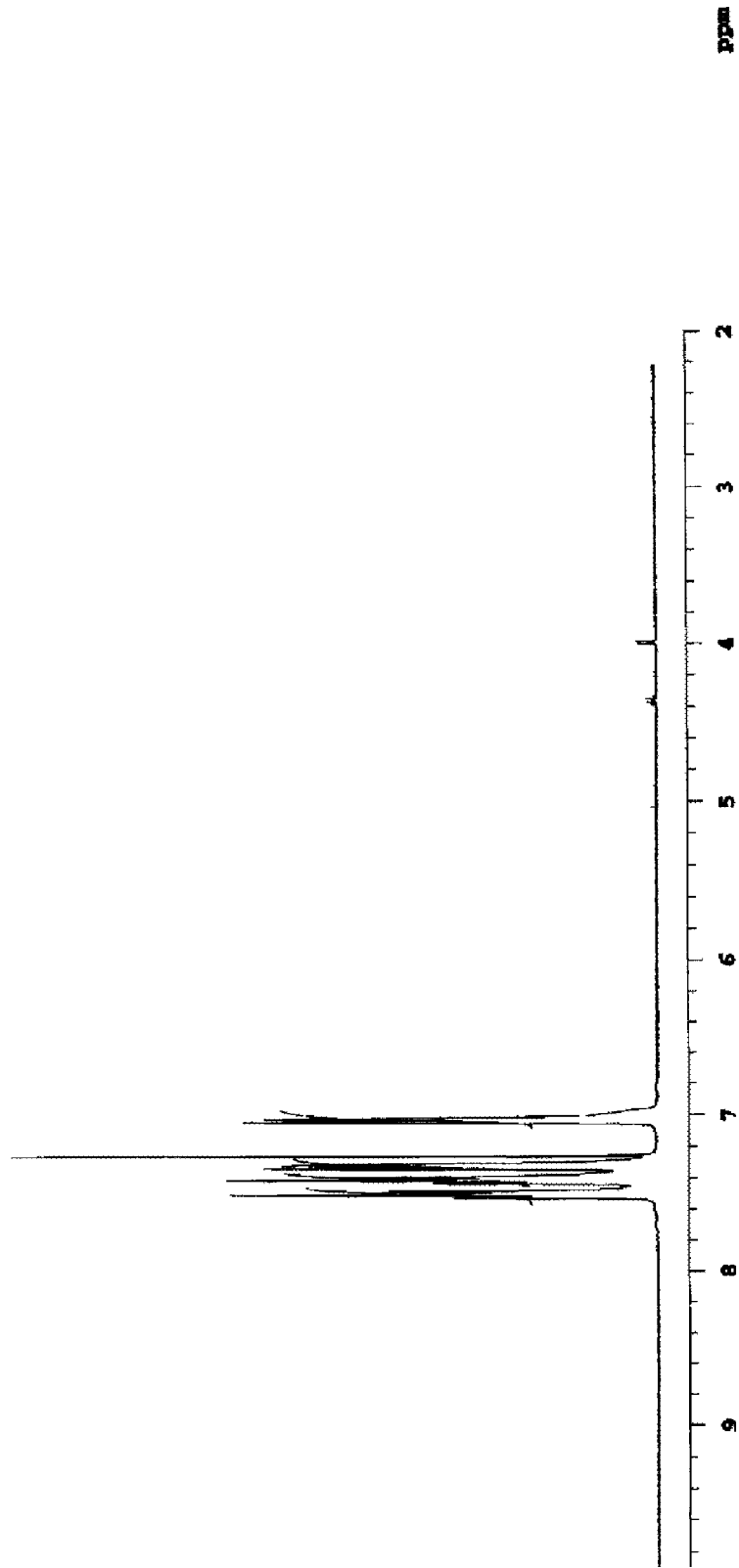
FIG. 11 shows a chart of $^1$H-NMR measurement of a polymer (BP6FBA-6FBA) obtained in Synthetic Example 6 of the present invention, consisting of BP6FBA and 6FBA.
Figure 12:
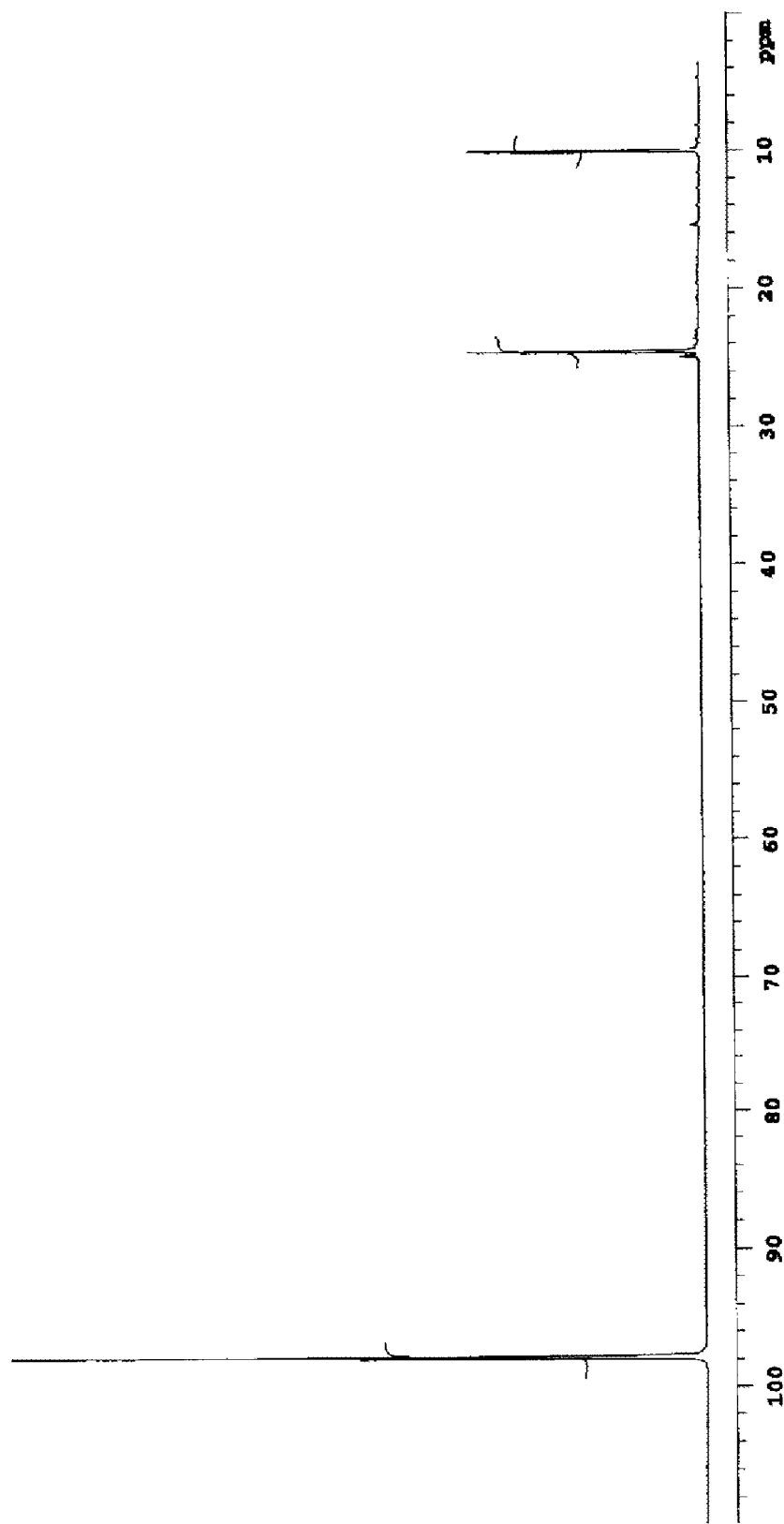
FIG. 12 shows a chart of $^{19}$F-NMR measurement of a polymer (BP6FBA-6FBA) obtained in Synthetic Example 6 of the present invention, consisting of BP6FBA and 6FBA.

BP6FBA 3.00 g (4.14 mmol), 6FBA 1.39 g (4.14 mmol), potassium carbonate 2.86 g (20.70 mmol), a molecular sieve 10.00 g and MEK 100 g were charged and reacted at 75° C. for 2 hours. After that, the reaction solution was added to 0.5 L of deionized water to obtain a polymer. The yield of the polymer was 85%. The charts of $^1$H-NMR and $^{19}$F-NMR measurement of the obtained polymer are shown in FIG. 11 and FIG. 12.

The obtained polymer had a number average molecular weight 16100. The polymer was also evaluated for thermal property and measured for transmittance and total luminous transmittance and evaluated for electric property. The results are shown in Tables 3, 4 and 5.

TABLE 3

| | Glass transition temperature(° C.) | 5% by weight loss(° C.) |
|---|---|---|
| Synthesis Example 4 | 214 | 470 |
| Synthesis Example 5 | 181 | 458 |
| Synthesis Example 6 | 175 | 459 |

TABLE 4

| | Transmittance (850 nm)(%) | Total luminous transmittance(%) |
|---|---|---|
| Synthesis Example 4 | 89.8 | 89.9 |
| Synthesis Example 5 | 90.1 | 90.5 |
| Synthesis Example 6 | 90.8 | 91.2 |

TABLE 5

| | dielectric constant (1 MHz) |
|---|---|
| Synthesis Example 4 | 3.05 |
| Synthesis Example 5 | 2.80 |
| Synthesis Example 6 | 2.69 |

EXAMPLES 2 TO 6 AND COMPARATIVE EXAMPLE 2

1 g each of the compounds synthesized in Synthesis Examples 2 to 6 was added to polymethyl methacrylate (PMMA) 2 g dissolved in toluene 18 g. Each mixture was cast on a glass plate and dried to obtain a film. Each film was evaluated for thermal property and measured for refractive index, and water absorption ratio. The results are shown in Tables 6 to 8. For comparison, PMMA alone was also measured. Thermal property evaluation, refractive index measurement, and water absorption measurement were carried out in the manner described later.

TABLE 6

| | | 5% by weight loss(° C.) | Glass transition on-set(° C.) |
|---|---|---|---|
| Example 2 | PMMA/BPDES | 296 | 104 |
| Example 3 | PMMA/BP6FBA | 304 | 101 |
| Example 4 | PMMA/BPDES-HF | 350 | 123 |
| Example 5 | PMMA/BPDES-6FBA | 347 | 117 |
| Example 6 | PMMA/BP6FBA-6FBA | 330 | 110 |
| Comparative Example 2 | PMMA alone | 300 | 120 |

TABLE 7

| | | 632.8 nm | 830 nm | 1310 nm | 1550 nm |
|---|---|---|---|---|---|
| Example 2 | PMMA/BPDES | 1.4992 | 1.4971 | 1.4863 | 1.4813 |
| Example 3 | PMMA/BP6FBA | 1.4888 | 1.4836 | 1.4770 | 1.4722 |
| Example 4 | PMMA/BPDES-HF | 1.5264 | 1.5189 | 1.5129 | 1.5105 |
| Example 5 | PMMA/BPDES-6FBA | 1.5053 | 1.4993 | 1.4931 | 1.4914 |
| Example 6 | PMMA/BP6FBA-6FBA | 1.4947 | 1.4893 | 1.4839 | 1.4825 |
| Comparative Example 2 | PMMA alone | 1.4903 | 1.4857 | 1.4815 | 1.4804 |

TABLE 8

| | | Water absorption ratio(%) |
|---|---|---|
| Example 2 | PMMA/BPDES | 0.79 |
| Example 3 | PMMA/BP6FBA | 0.23 |
| Example 4 | PMMA/BPDES-HF | 0.45 |
| Example 5 | PMMA/BPDES-6FBA | 0.38 |
| Example 6 | PMMA/BP6FBA-6FBA | 0.26 |
| Comparative Example 2 | PMMA alone | 1.15 |

SYNTHESIS EXAMPLE 7

Synthesis Of Di(Perfluorobenzoyl)Hydrazide (10F-BH)

Perfluorobenzoylchloride (PFBC) 23.5 g (102 mmol) and N-methyl-2-pyrrolidinone (NMP) 100 mL were charged into a 250 mL flask equipped with a dropping funnel and a nitrogen gas inlet tube. The flask was cooled to −10° C. and N$_2$H$_4$.H$_2$O 2.6 g (52 mmol) was dropwise added slowly to the flask under stirring condition. On completion of the dropping addition, the mixture was reacted at −10° C. for 6 hours. Next, the reaction mixture was added to excess water, filtered, and dried. The obtained product was recrystallized twice using methanol and water to produce a white crystal of 10F-BH (yield 63.4%). The melting point of 10F-BH was 270.3° C.

SYNTHESIS EXAMPLE 8

Synthesis Of Di(Perfluorooxadiazole) (10F-Oxadiazole)

Figure 13:
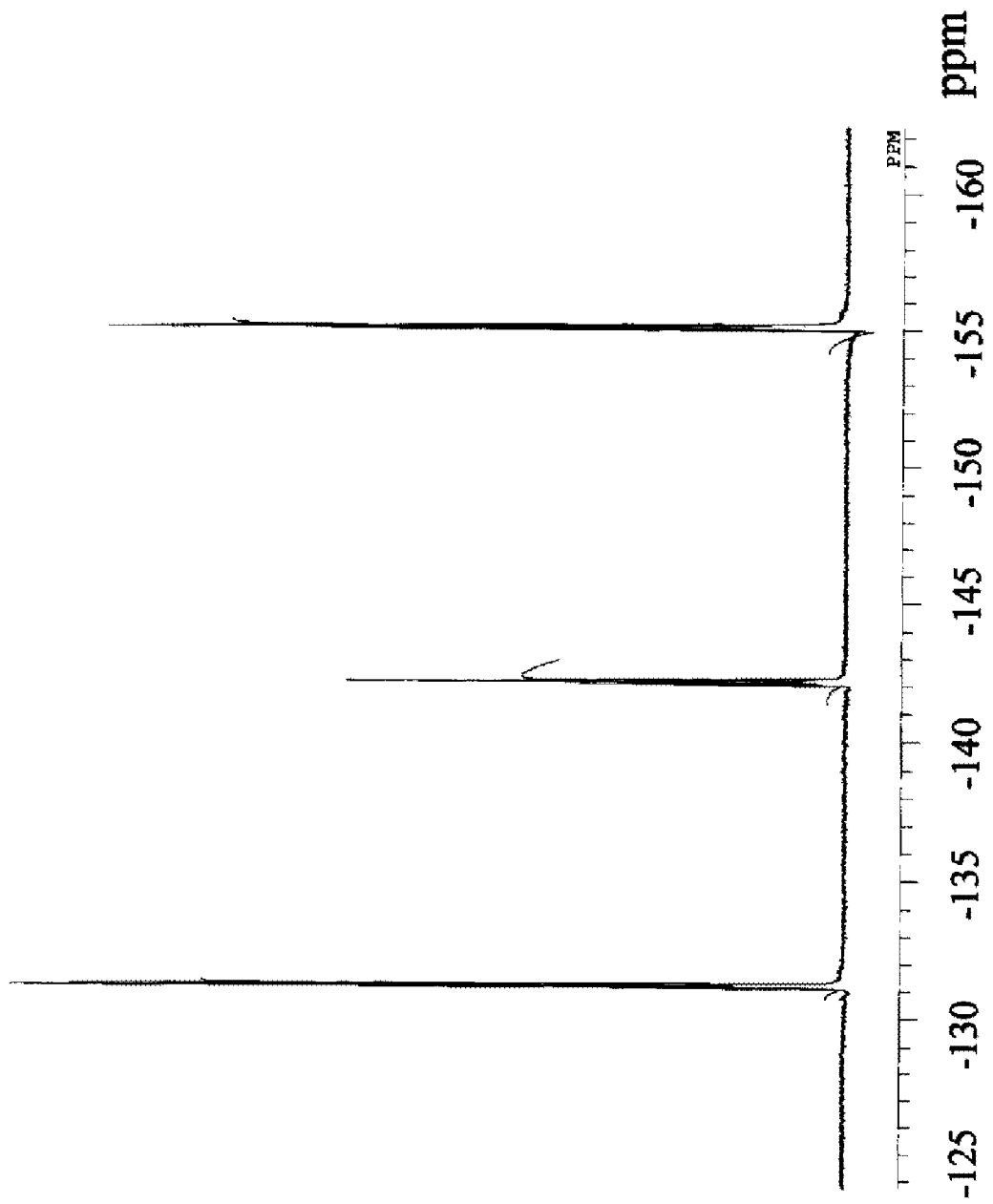
FIG. 13 shows a chart of $^{19}$F-NMR measurement of di(perfluorooxadiazole) (10F-oxadiazole) obtained in Synthetic Example 8 of the present invention.
Figure 14:
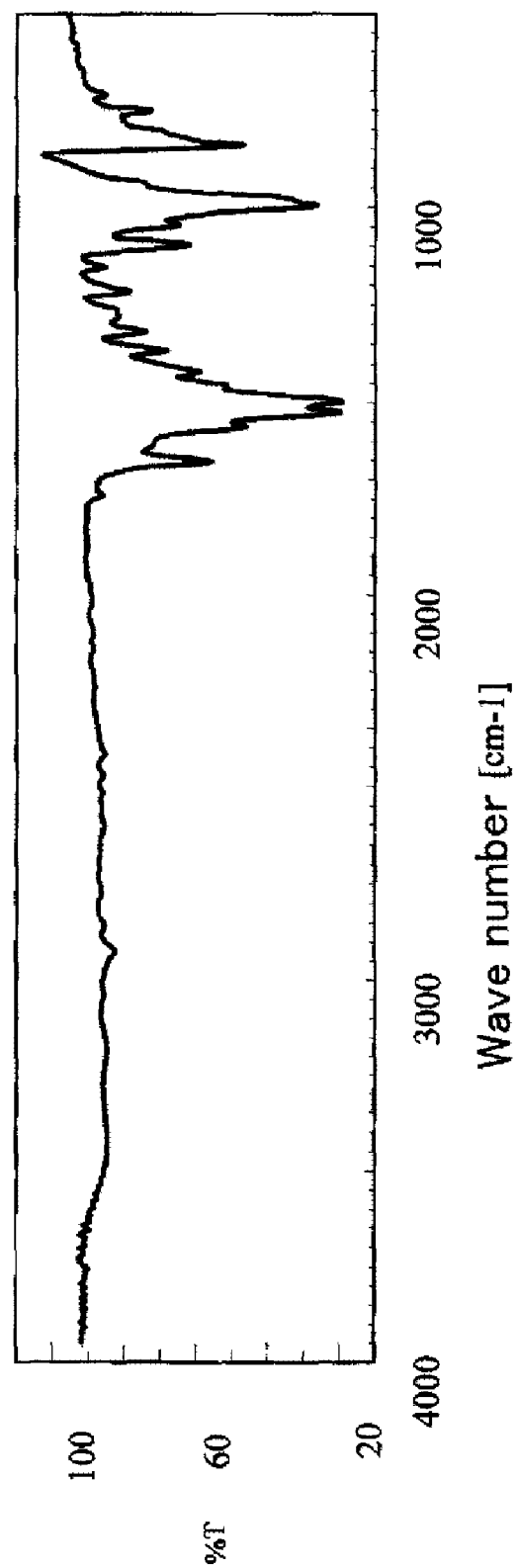
FIG. 14 shows a chart of IR measurement of di(perfluorooxadiazole) (10F-oxadiazole) obtained in Synthetic Example 8 of the present invention.

A 250 mL flask equipped with a reflux condenser was charged with 10F-BH 8.4 g (36.4 mmol), thionyl chloride 200 g, and pyridine 0.8 g and the mixture was refluxed for 3 hours under nitrogen current. After excess thionyl chloride was removed by distillation, the product was dried under reduced pressure for 3 hours. The obtained product was recrystallized using methanol to produce a white crystal of 10F-oxadiazole (yield 41.6%). The melting point of 10F-oxadiazole was 161.4° C. The obtained 10F-oxadiazole was measured for $^{19}$F-NMR and IR. The results are shown in FIG. 13 and FIG. 14.

SYNTHESIS EXAMPLE 9

Synthesis of a Condensation Polymer (8F-PO (6FBA)) of di(perfluorooxadiazole) (10F-oxadiazole) and hexafluorbisphenol A (6FBA)

A 50 mL flask equipped with a Dean-Stark trap containing toluene 1.5 g and a reflux condenser was charged with 6FBA 0.17 g (0.51 mmol), potassium carbonate 0.071 g (0.51 mmol) and NMP 1.5 g. The mixture was refluxed at 150° C. for 3 hours under nitrogen atmosphere and then dewatered and then toluene was removed by distillation. The product was cooled to 30° C. and mixed with 10F-oxadiazole 0.22 g (0.55 mmol). While being kept at 30° C., the mixture was reacted for 2 hours. On completion of the reaction, the reaction solution was cooled and while the reaction solution being fiercely stirred by a blender, water was added. The precipitated condensation polymer was separated by filtration and washed with distilled water and methanol and then, dried under reduced pressure. The produced condensation polymer was represented by the following formula (16).

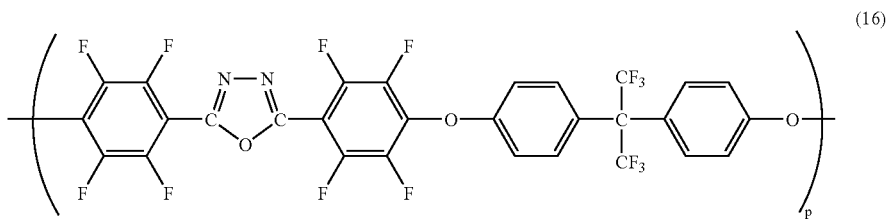

(16)

Figure 15:
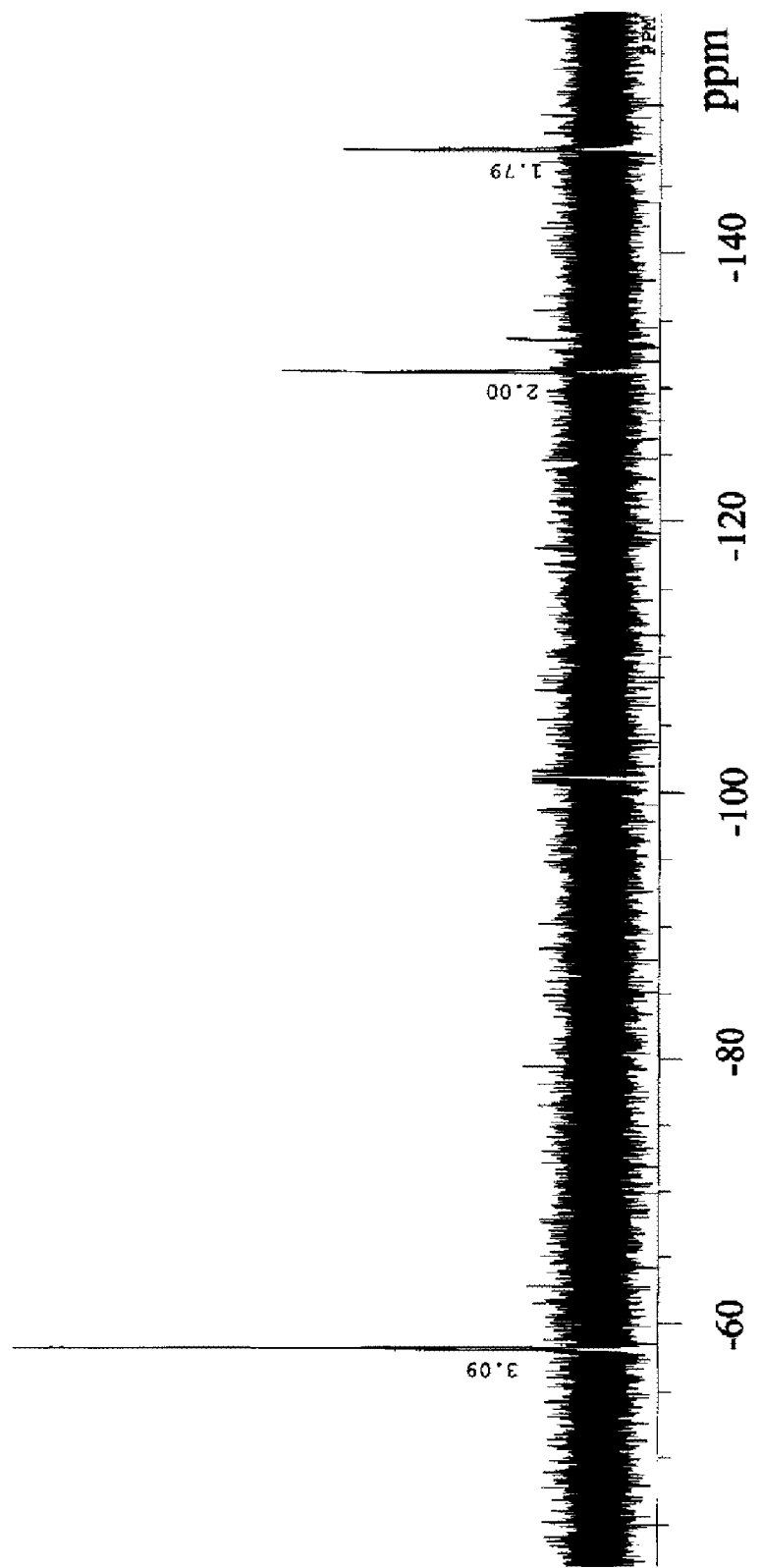
FIG. 15 shows a chart of $^{19}$F-NMR measurement of a condensation polymer (8F-PO(6FBA)) of di(perfluorooxadiazole) (10F-oxadiazole) and hexafluorbisphenol A (6FBA), obtained in Synthetic Example 9 of the present invention.
Figure 16:
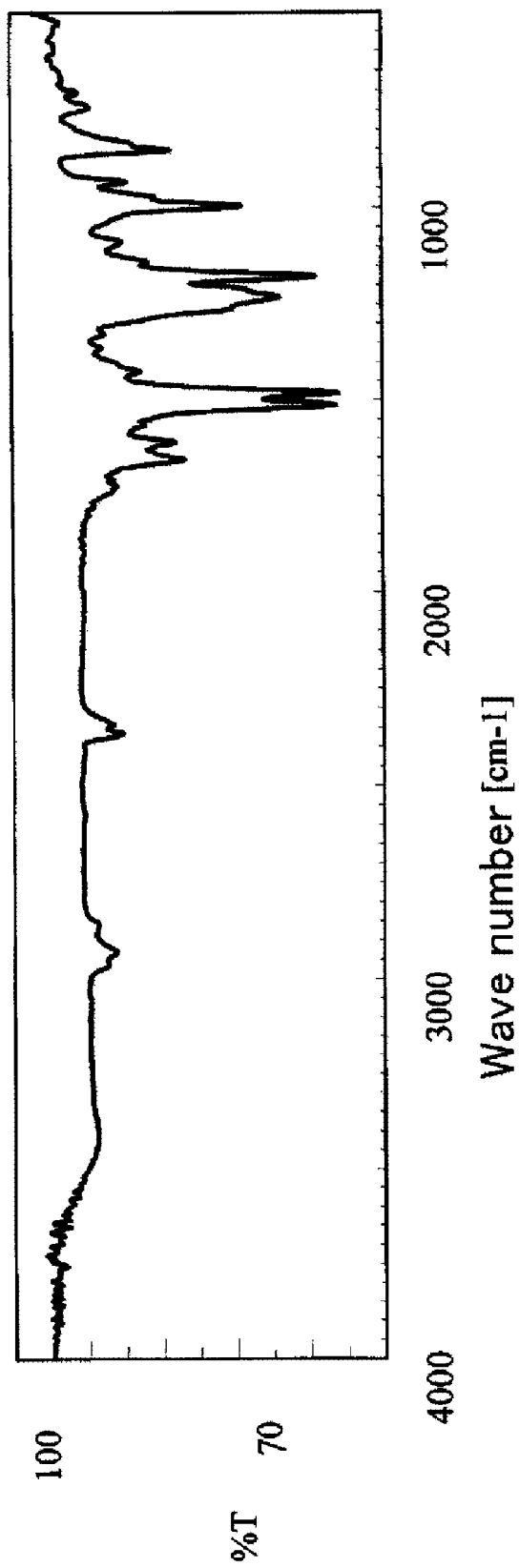
FIG. 16 shows a chart of IR measurement of a condensation polymer (8F-PO(6FBA)) of di(perfluorooxadiazole) (10F-oxadiazole) and hexafluorbisphenol A (6FBA), obtained in Synthetic Example 9 of the present invention.

The obtained condensation polymer was measured for $^{19}$F-NMR and IR. The results are shown in FIG. 15 and FIG. 16. The measurement results of yield and number average molecular weight are shown in Table 9.

The evaluation results of respective properties such as solubility in the respective solvents and the thermal property (glass transition temperature (Tg)), transmittance (transparency), water absorption ratio, and dielectric constant of the produced 8F-PO are shown in Table 10 to Table 15. The evaluation methods of the respective properties are as follows. In Table 10, DMAc stands for dimethylacetamide and THF stands for tetrahydrofuran.

TABLE 9

| Polymer | Yield(%) | Number average molecular weight |
|---|---|---|
| 8F-PO (6FBA) | 95.0 | 22600 |

TABLE 10

| Polymer | NMP | DMAc | THF | CHCl₃ | Toluene |
|---|---|---|---|---|---|
| 8F-PO (6FBA) | + | + | + | + | +− |

TABLE 11

| Polymer | Tg(° C.) |
|---|---|
| 8F-PO (6FBA) | 196 |

TABLE 12

| Polymer | Measured wavelength(nm) | Trancemittance(%) |
|---|---|---|
| 8F-PO (6FBA) | 850 | 89.5 |

TABLE 13

| Polymer | Total luminous transmittance(%) |
|---|---|
| 8F-PO (6FBA) | 89.0 |

TABLE 14

| Polymer | Water absorption ratio(%) |
|---|---|
| 8F-PO (6FBA) | Less than 0.05 |

TABLE 15

| Polymer | Measured frequency(Hz) | Dielectric constant |
|---|---|---|
| 8F-PO (6FBA) | 1000000 | 3.2 |

[Measurement of $^1$H-NMR and $^{19}$F-NMR Spectrum]

SYNTHESIS EXAMPLE 1 TO 6

Using Unity Plus 400 (manufactured by Varian), spectrum was measured by using CDCl₃ solvent, and analyzed the structure. As for $^1$H-NMR spectrum measurement, hydrogen atom of tetramethylsilane (TMS) was used as internal standard which was positioned in 0 ppm. And as for $^{19}$F-NMR spectrum, in Synthesis Example 1, hexafluorobenzonitrile was used as internal standard and in Synthesis Example 2 to 6, hexafluorobenzene was used as internal standard.

SYNTHESIS EXAMPLE 8 AND 9

Using Varian Gemini 200 (manufactured by Varian), spectrum was measured at 200 MHz. DMSO was used as measurement solvent.

[Measurement of IR Spectrum]

Using FT/OR-350 type Fourier transform spectrophotometer manufactured by JASCO Corporation, IR spectrum was measured by KBr pellet method.

[Thermal Property Evaluation]

SYNTHESIS EXAMPLE 1 to 6 AND EXAMPLE 2 to 6, COMPARATIVE EXAMPLE 2

Using Shimadzu Simultaneous TG/DTA Instrument (manufactured by Shimadzu Corporation), decomposition temperature (the temperature at weight decrease of 2% by weight) of Synthsis Example 1, the melting point of Synthesis Example 2 and 3, the glass transition temperature and the temperature at weight decrease(5% by mass loss) of Synthesis Example 4 to 6, and the glass transition on-set (starting temperature of the glass transition) and the temperature at weight decrease(5% by mass loss) of Example 2 to 6 and Comparative Example 2 were measured. The heating rate was at 10° C./min under nitrogen atmosphere.

SYNTHESIS EXAMPLE 9

Using a differential scanning calorimeter (DSC-7) manufactured by Perkin Elmer, the thermal property evaluation was carried out by measuring the glass transition temperature (Tg) at 20° C./min under nitrogen atmosphere.

[Measurement of Number Average Molecular Weight]

Using HLC-8120 GPC (manufactured by Tosoh Corporation) and column: G-5000HXL+GMHXL-L, the measurement was carried out. THF was used as a development solvent at 1 mL/min flow rate and polystyrene was used as standard and the number average molecular weight was measured by polystyrene conversion.

[Water Absorption Ratio]

The films produced by the same manner as in Example 1 were immersed in water at 25° C. for 72 hours and the weight alteration was measured to calculate water absorption ratio for Example 1 and Comparative Example 2.

The films produced were dried at 110° C. for 15 hours and then the films were immersed in water at 25° C. for 48 hours and the weight alteration was measured to calculate water absorption ratio for Examples 2 to 6 and Comparative Example 2 and Synthesis Example 9.

[Refractive Index Measurement]

Using Prism Coupler SPA-4000 (manufactured by SAIRON TECHNOLOGY), the refractive index at 632.8 nm, 830 nm, 1310 nm and 1550 nm was measured.

[Measurement of Transmittance]

Using Shimadzu UV-3100 (manufactured by Shimadzu Corporation), the transmittance at 850 nm was measured. The materials in form of 30 μm films were used for the measurement.

[Total Luminous Transmittance, Haze]

Colorimetry color difference meter NDH-1001 DP model (manufactured by Nippon Denshoku Kogyo Co., Ltd.) was employed for the measurement.

Measurements for total luminous transmittance and haze for Example 1 and Comparative Example 1 were carried out with 50 μm-thick films produced by the same manner as in Example 1. In Synthesis Example 4 to 6 and 9, total luminous transmittance in form of 30 μm films were used for the measurement of total luminous transmittance.

[Evaluation of Electric Property (Measurement of Dielectric Constant)]

The dielectric constant was measured using Impedance Analyzer HP 4294A8 (manufactured by HEWLETT PACKERD Co., Ltd.)

[Measurement of Solubility]

Each solvent 3 mL at 25° C. was mixed with 8F-PO (6FBA) 0.1 g and stirred for 10 minutes to measure the solubility. The evaluation standards were as follows.

+: dissolved

+−: partially dissolved

From the experimental results shown in Tables 1 and 2, it was verified that when the fluorine-containing compound of the present invention represented by the formula (1) was added to a transparent resin material, it becomes possible to effectively make the transparent resin material low in a water absorbing property without deterioration of the transparency of the transparent resin material.

From the experimental results shown in Tables 3 to 8, it was verified that the fluorine-containing aryl ester polymer of the present invention containing a repeating unit represented by the formula (6) had high heat resistance and transparency, and had excellent optical properties and electrical properties.

In addition, it was verified that, when the fluorine-containing ester compound of the present invention represented by the formula (3) and/or the fluorine-containing aryl ester polymer of the present invention containing a repeating unit represented by the formula (6) were added to the resin, it becomes possible to make the resin low in a water absorbing ratio and to control the refractive index of the resin and also, it was verified that the addition was effective in suppressing the lowering the heat resistance.

From the experimental results shown in Tables 9 to 15, it was verified that a polymer having a structure unit of fluorine-containing oxadiazole represented by the formula (10) of the present invention had good solubility in various solvents and also had high heat resistance and water repellency and was superior in optical properties and electrical properties such as transparency and a dielectric constant.

The present application claims priority under 35 U.S.C. §119 to Japanese Patent Application No. 2004-160154, filed May 28, 2004, entitled "TRANSPARENT RESIN MATERIAL", Japanese Patent Application No. 2004-226815, filed Aug. 3, 2004, entitled "FLUORINE-CONTAINING COMPOUND", Japanese Patent Application No. 2004-344273, filed Nov. 29, 2004, entitled "OPTICAL AND ELECTRICAL PARTS MATERIAL USING FLUORINE-CONTAINING OXADIZOLE COMPOUND", and Japanese Patent Application No. 2004-349160, filed Dec. 1, 2004, entitled "FLUORINE-CONTAINING ESTER COMPOUND, FLUORINE-CONTAINING ARYL ESTER POLYMER AND PRODUCTION METHOD THEREOF AND RESIN COMPOSITION COMPRISING THEREOF".

The invention claimed is:

1. A fluorine-containing aryl ester polymer which contains a repeating unit represented by the following formula (6):

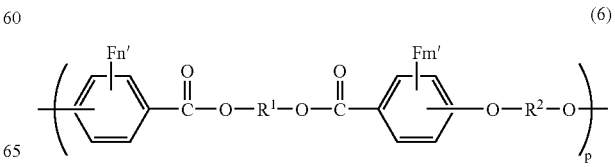

in the formula, m' and n' are same or different and each represents the number of fluorine atoms bonded to a benzene ring and is an integer of 0 to 4 and m'+n' is an integer of 1 or more; $R^1$ and $R^2$ are same or different and each represents a divalent organic group having 1 to 150 carbon atoms; and p is 1 to 5000.

2. The fluorine-containing aryl ester polymer according to claim 1 which comprises a repeating unit represented by the following formula (7):

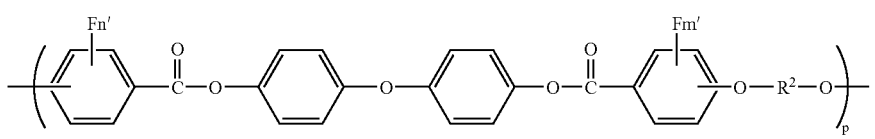
(7)

in the formula, m' and n' are same or different and each represents the number of fluorine atoms bonded to a benzene ring and is an integer of 0 to 4 and m'+n' is an integer of 1 or more; $R^2$ represents a divalent organic group having 1 to 150 carbon atoms; and p is 1 to 5000, and/or a repeating unit represented by the following formula (8):

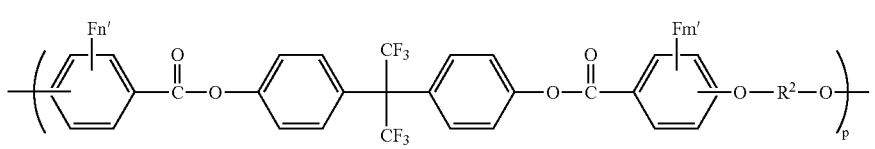
(8)

in the formula, m' and n' are same or different and each represents the number of fluorine atoms bonded to a benzene ring and is an integer of 0 to 4 and m'+n' is an integer of 1 or more; $R^2$ represents a divalent organic group having 1 to 150 carbon atoms; and p is 1 to 5000.

3. A body formed from a composition which comprises the fluorine-containing aryl ester polymer according to claim 1.

4. A fluorine-containing ester compound suitable for obtaining the fluorine-containing aryl ester polymer according to claim 1 wherein the fluorine-containing ester compound is represented by the following formula (3):

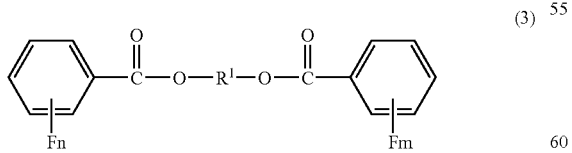
(3)

in the formula, m and n are same or different and each represents the number of fluorine atoms bonded to a benzene ring and is an integer of 0 to 5 and m+n is an integer of 1 or more; and $R^1$ represents a divalent organic group having 1 to 150 carbon atoms.

5. A method of producing a fluorine-containing aryl ester polymer, wherein said method comprises polymerizing the fluorine-containing ester compound according to claim 4 with a dihydroxy compound represented by the following formula (9)

$$HO-R^2-OH \qquad (9),$$

in the formula, $R^2$ represents a divalent organic group having 1 to 150 carbon atoms, in the presence of a basic catalyst.

6. The fluorine-containing ester compound according to claim 4, wherein said fluorine-containing ester compound is represented by the following formula (4) or (5):

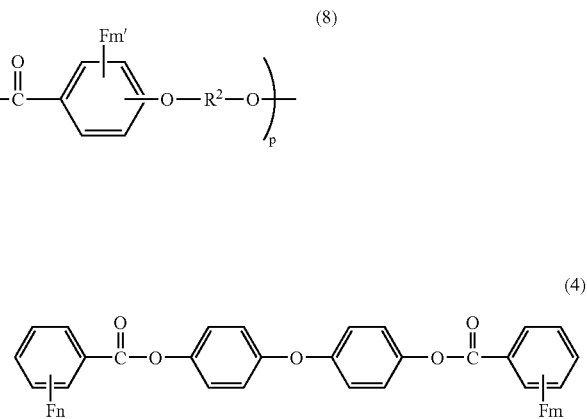

in the formula, m and n are same or different and each represents the number of fluorine atoms bonded to a benzene ring and is an integer of 0 to 5 and m+n is an integer of 1 or more.

* * * * *